(12) United States Patent
Cheung et al.

(10) Patent No.: US 7,241,598 B2
(45) Date of Patent: Jul. 10, 2007

(54) FRAME-SHIFTING PCR FOR GERMLINE IMMUNOGLOBULIN GENES RETRIEVAL AND ANTIBODY ENGINEERING

(75) Inventors: Wing-Tai Cheung, Hong Kong (CN); Man Cheng, Hong Kong (CN)

(73) Assignee: The Chinese University of Hong Kong, Hong Kong SAR (CN)

( * ) Notice: Subject to any disclaimer, the term of this patent is extended or adjusted under 35 U.S.C. 154(b) by 158 days.

(21) Appl. No.: 10/880,238

(22) Filed: Jun. 29, 2004

(65) Prior Publication Data

US 2005/0287538 A1    Dec. 29, 2005

(51) Int. Cl.
*C12P 19/34* (2006.01)
*C12P 21/00* (2006.01)

(52) U.S. Cl. .................................. 435/91.2; 435/70.1

(58) Field of Classification Search .................... None
See application file for complete search history.

(56) References Cited

U.S. PATENT DOCUMENTS

| 5,338,669 | A | * | 8/1994 | Gillies | 435/69.1 |
| 5,658,727 | A | * | 8/1997 | Barbas et al. | 435/6 |
| 5,837,242 | A | * | 11/1998 | Holliger et al. | 424/136.1 |
| 2004/0081638 | A1 | * | 4/2004 | Kyle | 424/93.2 |

OTHER PUBLICATIONS

Wagle et al., CD19 regulates B cell antigen receptor-mediated MHC class II antigen processing. Vaccine (2000) 18: 376-386.*
Buck et al., Design strategies and performance of custom DNA sequencing primers. BioTechniques (1999) 27: 528-536.*

\* cited by examiner

*Primary Examiner*—Jeffrey Fredman
*Assistant Examiner*—David C. Thomas
(74) *Attorney, Agent, or Firm*—Occhiuti, Rohlicek & Tsao LLP

(57) ABSTRACT

A method for preparing an antigen-specific antibody by constructing a library of phage-displayed single chain variable fragment of an antibody with a novel frame-shifting PCR is disclosed. Also disclosed is a method for preparing a clone for producing an antigen-specific antibody.

19 Claims, 9 Drawing Sheets

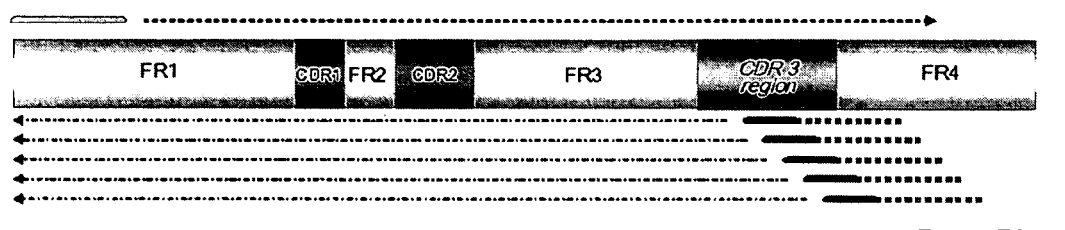
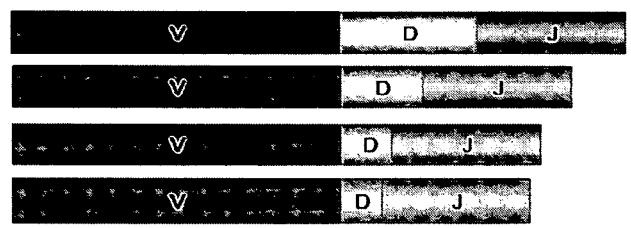
FIG. 1
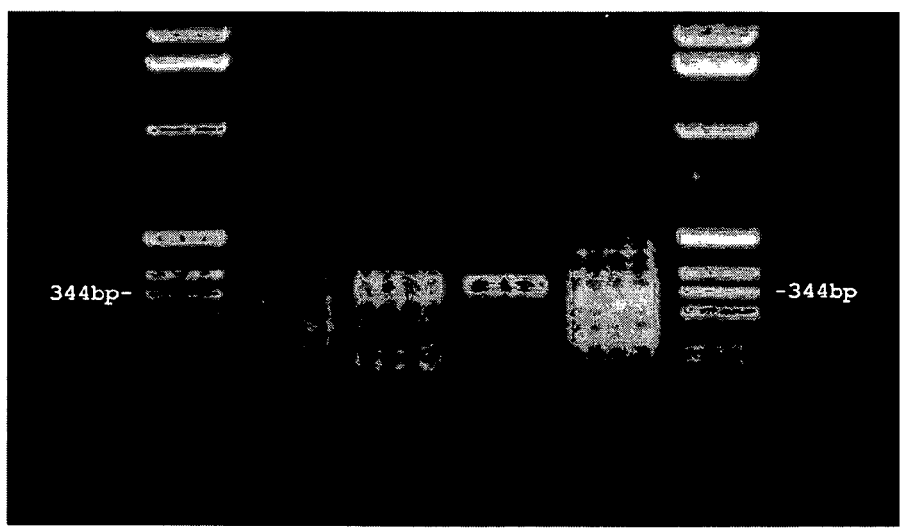
FIG. 2

FIG. 4

| Clones | VH FR1 | VH CDR1 | VHFR2 |
|---|---|---|---|
| L3H11A-VH | GEA-GAELVKPGASVKLSCTAS | GFNIKDTYMH | WVKQRPEQGLEWIG |
| L3E4C-VH | GAAAGAELVKPGASVKLSCTAS | GFNIKDTYMH | WVKQRPEQGLEWIG |
| L3E2C-VH | GAAGPELVRSGASVKLSCTAS | GFNIKDYYMH | WVKQRPEQGLEWIG |
| L3C4C-VH | GAAGAELVRSGASVKLSCTAS | GFNIKDYYMH | WVKQRPEQGLEWIG |
| L3B5C-VH | QVLLLE-SGGGLVQPGGSMKLSCAAS | GFTFSDAWMD | WVRQSPEKGLEWVA |
| L3A9C-VH | SDAAGGGLVQPGGSMKLSCVAS | GFTFSNYWMN | WVRQSPEKGLEWVA |
| L3A6C-VH | GDAAAGLVQPGGSMKLSCVAS | GFTFSNYWMN | WVRQSPEKGLEWVA |
| L3G11C-VH | GAA-GGGLVQPGGSMKLSCVAS | GFTFSNYWMN | WVRQSPEKGLEWVA |
| L3B10B-VH | GDAGGGGLVQPGGSMKLSCVAS | GFTFSNYWMN | WVRQSPEKGLEWVA |
| L3E6C-VH | GAA-GGLVQPGGSMKLSCVAS | GFTFSNYWMN | WVRQSPEKGLEWVA |
| L3G7C-VH | GAA-GGLVQPGGPMKLSCVAS | GFTFSNYWMS | WVRQSPEKGLEWVA |
| L3D11C-VH | VKLEQSGPELVKPGASVKISCKAS | GYSFTGYFMN | WVMQSHGKSLEWIG |

| Clones | VL FR1 | VL CDR1 | VLFR2 |
|---|---|---|---|
| L3A6C-VL | EIVMTQTPASLSMAIGEKVTIRC | ITSTDIDDDMN | WYQQKPGEPPNLL |
| L3E6C-VL | KSVMTQTPLTLSVTIGQPASISC | KSSQSLLDSDGKTYLN | WLLQRPGQSPKRL |
| L3A9C-VL | DVVLTQTPLTLSVTIGQPASISC | KSSQSLLDSDGKTYLN | WLLQRPGQSPKRL |
| L3B5C-VL | DVVLTQTPASLAVSLGQRATISC | RASESVDNYGISFMN | WFQQKPGQPPKLL |
| L3C6C-VL | DVVITQTTASLAVSLGQRATISC | RASESVDNYGISFMN | WFPTETRTATQTPHLCC |
| L3E4C-VL | EIVITQSPASLAVSLGQRATIFC | RASQSVDYNGISYMH | WFQQKPGQPPKLL |
| L3B10B-VL | VVMTQSPAIMSASLGERVTMTC | TASSSVSSSYLH | WYQQKPGSSPKLW |
| L3G7C-VL | DIVLTQTTAIMSASLGERVTMTC | TASSSVSSSYLH | WYQQKPGSSPKLW |
| L3D11C-VL | IVLTQTTAIMSASLGERVTMTC | TASSSVSSSYLH | WYQQKPGSSPKLW |
| L3E2C-VL | DVVMTQTTAIMSASLGERVTMTC | TASSSVSSSYLH | WYQQKPGSSPKLW |
| L3H11A-VL | DVVLTQTTAIMSASLGERVTMTC | TASSSVSSSYLH | WYQQKPGSSPKLW |
| L3D5C-VL | EVVITQTPAIMSASLGERVTMTC | TASSSVSSSYLH | WYQQKPGSSPKLW |
| L3A8B-VL | DVVLTQTTAIMSASLGERVTMTC | TASSSVSSSYLH | WYQQKPGSSPKLW |
| L3G11C-VL | EIVMTQSTAIMSASLGERVTMTC | TASSSVSSSYLH | WYQQKPGSSPKLW |

FIG. 6A

| Clones | VH CDR2 | VH FR3 |
|---|---|---|
| L3H11A-VH | RIDPANGNTKYDPKFQG | KATITADTSSNTAYLQLSSLTSGDTAVYYCAS |
| L3E4C-VH | RIDPANGNTKYDPKFQG | KATITADTSSNTAYLQLSSLTSEDTAVYYCAR |
| L3E2C-VH | WIDPENGDTEYAPKFQG | KATMTADTSSNTAYLQLSSLTSEDTAVYYCSG |
| L3C4C-VH | WIDPENGDTEYAPKFQG | KATMTADTSSNTAYLQLSSLTSEDTAVYYCNA |
| L3B5C-VH | EIRSKANNHATYYAESVKG | RFTISRDDSKSSVYLQMNSLRAEDTGIYYCTR |
| L3A9C-VH | EIRLKPNNYATHYAESVKG | RFTISRDDSKSSVYLQMNNLRAEDTGIYYCTR |
| L3A6C-VH | EIRLKSNNYAIHYAESVKG | RFTISRDDSKSSVYLQMNNLRAEDTGIYYCTR |
| L3G11C-VH | EIRLKSNNYATHYAESVKG | RFTISRDDSKSSVYLQMNNLRHVGPRNLCHCLL |
| L3B10B-VH | EIRLKSNNYATHYAESVKG | RFTISRDDSKSSVYLQMNNLRAEDTGIYYCTR |
| L3E6C-VH | EXRLKSNNYATHYAESVKG | RFTISRDDSKSSVYLQMNNLRAEDTGIYYCTR |
| L3G7C-VH | EIRLKSNNYATHYAESVKG | RFTISGDDSKSSVYLQMNSLRAEDTGIYYCTR |
| L3D11C-VH | RINPYNGDTFYNQKFKG | KATLTVDKSSSTAHMELRSLASEDSAVYYCAR |

| Clones | VL CDR2 | VL FR3 |
|---|---|---|
| L3A6C-VL | ISE | DNTLRPGVPSRFSSSGYGTDFVFTIENMLSEDAADYYC |
| L3E6C-VL | IYLVSKL | DSGVPDRFTGSGSGTDFTLKISRVEAEDLGVYYC |
| L3A9C-VL | IYQVSKL | DSGVPDRFTGSGSGTDFTLKISRVEAEDLGVYYC |
| L3B5C-VL | IYAASNQ | GSGVPARFSGSGSGTDFSLNIHPMEKDDTAMYFC |
| L3C6C-VL | LQPRIRG | PCHV-WQWVWDRLSLNIHPMEEDDTAMYFCQQS |
| L3E4C-VL | IYAASNL | ESGIPARFSGSGSGTDFTLNIHPVEEEDAATYYC |
| L3B10B-VL | IYSTSNL | ASGVPARFSGSGSGTSYSLTISSMEAEDAATYYC |
| L3G7C-VL | IYSTSNL | ASGVPARFSGSGSGTSYSLTISSMEAEDAATYYC |
| L3D11C-VL | IYSTSNL | ASGVPARFSGSGSGTSYSLTISSMEAEDAATYYC |
| L3E2C-VL | IYSTSNL | ASGVPARFSGSGSGTSYSLTISSMEAEDAATYYC |
| L3H11A-VL | IYSTSNL | ASGVPARFSGSGSGTSYSFTISSMEAEDAATYYC |
| L3D5C-VL | IYSTSNL | ASGVPARFSGSGSGTSYSLTISSMEAEDAATYYC |
| L3A8B-VL | IYSTSNL | ASGVPARFSGSGSGTSYSLTISSMEAEDAAAYYC |
| L3G11C-VL | IYSTYNL | ASGVPARFSGSGSGTSHSLTISSMEAEDAATYYC |

FIG. 6B

| Clones | VH CDR3 | VH FR4 |
|---|---|---|
| L3H11A-VH | NRDWFAL | WGPGTLLTVSS |
| L3E4C-VH | TDYPFYAMVVGWRNYTHRLL | -------- |
| L3E2C-VH | GAKEPLSLSL | -------- |
| L3C4C-VH | PFYDG-PLVCWLGSRNSAHCLL | -------- |
| L3B5C-VH | HPGHRLR | -------- |
| L3A9C-VH | PGYRYDRHTGAQAPRSLSP | -------- |
| L3A6C-VH | RNWYFGV | WGQGTPLTVSA |
| L3G11C-VH | -------- | -------- |
| L3B10B-VH | NYTHCLR | -------- |
| L3E6C-VH | RNWYFDY | WGEGHPSHCLL |
| L3G7C-VH | DYGYDGD | WGAGTSLTVSA |
| L3D11C-VH | VGVRNYFDI | WGPGTSVTVSA |

| Clones | VL CDR3 | VL FR4 |
|---|---|---|
| L3A6C-VL | LQSDNLPLDVRRRESWR | --------- |
| L3E6C-VL | WQGTHFPVT | FGAGTRLEI |
| L3A9C-VL | WQGT-LRSVVAQNWR | --------- |
| L3B5C-VL | QQVRRFPDT | FGAGTRLEI |
| L3C6C-VL | KEVPVNIRRRHKAGD | --------- |
| L3E4C-VL | QQSIEDPYT | FGGGTKLEI |
| L3B10B-VL | HQYHRSLGT | FGAGTKLEI |
| L3G7C-VL | HQYHRSPDT | FGAGTRLEI |
| L3D11C-VL | HQYHRSPGHVRRRDKTGN | --------- |
| L3E2C-VL | HQYHRSPPDIRRRHKTGN | --------- |
| L3H11A-VL | HQYHRSPRNIRRRHQTGN | --------- |
| L3D5C-VL | HQYHRSTHVRWGHKAGD | --------- |
| L3A8B-VL | QQYHSYPPDT | FGGGTKLEI |
| L3G11C-VL | HQYHRSPFT | FGEGTRLEI |

FIG. 6C

FRAME-SHIFTING PCR FOR GERMLINE IMMUNOGLOBULIN GENES RETRIEVAL AND ANTIBODY ENGINEERING

BACKGROUND OF THE INVENTION

1. Field of the Invention

The present invention relates to a method for preparing an antibody, particularly to a method for preparing an antigen-specific antibody by constructing a library of phage-displayed single chain variable fragment (ScFv) of an antibody using a novel frame-shifting PCR step.

2. Description of the Related Art

Monoclonal antibody (mAb) is mainly derived by cell fusion as described originally by Kohler and Milstein (1975). Owing to the broad application and wide perspective of the monoclonal antibody, important advances in design, selection, and production of engineered antibodies have been made. The traditional method for recombinant mAb construction like hybridoma technology has many limitations, such as duration, stability and class manipulation (Harlow and Lane, (1988) Monoclonal antibody: A laboratory manual pp. 141–149). Although new technology like the display of antibody fragments on the surface of filamentous phages and the subsequent selection of antibodies have been proved as an effective tool for the isolation of antigen specific antibodies (Barbas, C. F., Kang, A. S., Lerner, R. A. & Benkovic, S. J. (1991), Assembly of combinatorial antibody libraries on phage surfaces: the gene III site, Proc. Natl. Acad. Sci., USA 88, 7978–7982; Marks, J. D., (1992), By-passing immunization: building high affinity human antibodies by chain shuffling, Bio/Technology, 10, 779–783; Nissim, A. (1994), Antibody fragments from a 'single pot' phage display library as immunochemical reagents, EMBO J. 13, 692–698), it still has limitations. The library of phage-displayed single chain variable fragment (ScFv) of the antibody has been used for deriving tailor-made antigen-specific monoclonal antibody in the last decade. Furthermore, affinity enhancement of ScFv can be achieved by in vitro mutation.

In general, the affinity of isolated antibodies is proportional to the initial size of the library used for selection. Using mRNA as an enriched source of expressed and spliced antibody genes neglects the allelic exclusive genes so as half of the potential genes. Hence, the diversity of the library used for selection becomes limited. Moreover, the gene loss will happen in both self-intolerance gene elimination and gene inactivation during maturation of B-lymphocytes. Finally, the other problem that needs to be considered is the existence of non-functional genes. These genes refer to Ab genes containing stop codon(s) in their segments, either naturally or created by the vague rearrangement processes during the somatic recombination.

SUMMARY OF THE INVENTION

To overcome the drawbacks in the prior art, accordingly, one aspect of the invention provides a method for preparing a clone for producing an antigen-specific antibody, which comprises the steps of:
a) extracting genomic DNAs of lymphocytes from a mammalian immunized with a specific antigen;
b) recovering variable regions of immunoglobulin heavy and light chains from the genomic DNAs;
c) amplifying the variable regions using a frame-shifting PCR;
d) introducing both an adaptor and a linker to the variable regions obtained in step c);
e) linking the variable regions of immunoglobulin heavy and light chains obtained in step d) by an overlap-extensive PCR to obtain single-chain variable fragments; and
f) introducing the single-chain variable fragments into a host cell to form a clone.

Another aspect of the invention is to provide a method for preparing an antigen-specific antibody, comprising the step of expressing a clone prepared define herein.

Still another aspect of the present invention pertains to a method for retrieving either $V_{L-\kappa}$ or $V_H$ genes from a germline DNA comprising the steps of:
a) extracting genomic DNAs of lymphocytes from a mammalian immunized with a specific antigen or from a non-immunized mammalian;
b) recovering variable regions of immunoglobulin heavy and light chains from the genomic DNAs; and
c) amplifying the variable regions using a frame-shifting PCR to produce $V_{L-\kappa}$ or $V_H$ genes of variable lengths or sequences.

Yet another aspect of the present invention provides a method for constructing a library of the $V_{L-\kappa}$ or $V_H$ genes from a gernomic DNA comprising the steps of:
a) extracting lymphocytic genomic DNAs from a mammalian immunized with a specific antigen or from a non-immunized mammalian;
b) recovering variable regions of immunoglobulin heavy and light chains from the genomic DNAs using a semi-nested PCR;
c) amplifying the variable regions using a frame-shifting PCR to produce $V_{L-\kappa}$ or $V_H$ genes of variable lengths or sequences; and
d) cloning the $V_{L-\kappa}$ or $V_H$ genes into a vector.

The procedure of extracting lymphocytic genomic DNAs from a mammalian is kwon well to those skilled in the art. The mammalian may be mice, rabbits, dogs and human being. In a preferred embodiment of the invention, the mammalian is a mouse, and the lymphocytes are lymphocytic CD19$^+$ cells.

Preferably, the vector used in the invention is a TOPO TA vector.

BRIEF DESCRIPTION OF THE DRAWINGS

FIG. 1 shows schematic diagram of a frame-shifting PCR.

FIG. 2 shows a semi-nested and frame-shifting PCR amplification of Ig.

FIG. 4 shows frame-shifting PCR verification: nucleotide sequence alignment of κ-light chain variable region of Ig genes derived from non-immunized mouse splenocytic genomic DNA (SEQ ID NOs 1–28, respectively). Sequences are frame-shifted $V_{L-\kappa}$ genes which are subdivided into 7 families as shown in FIG. 3A, suggesting diversity-enhancement within the CDR3 region.

FIGS. 6A, 6B and 6C shows amino acid sequence alignment of heavy chain and light chain variable regions of isolated phOx-spcific ScFv (SEQ ID NOs 29–193, respectively). Alignment result of different ScFv clones indicates subdivision into different families and significant sequence variations within the CDR3 region.

FIGS. 7A and 7B show result of phageELISA and competitive phageELISA, in which FIG. 7A shows dose response of candidate clones and FIG. 7B shows normalized competitive phageELISA of phOx-specific clones with the use of phOx as free ligand.

DETAILED DESCRIPTION OF THE INVENTION

Figure 3A:
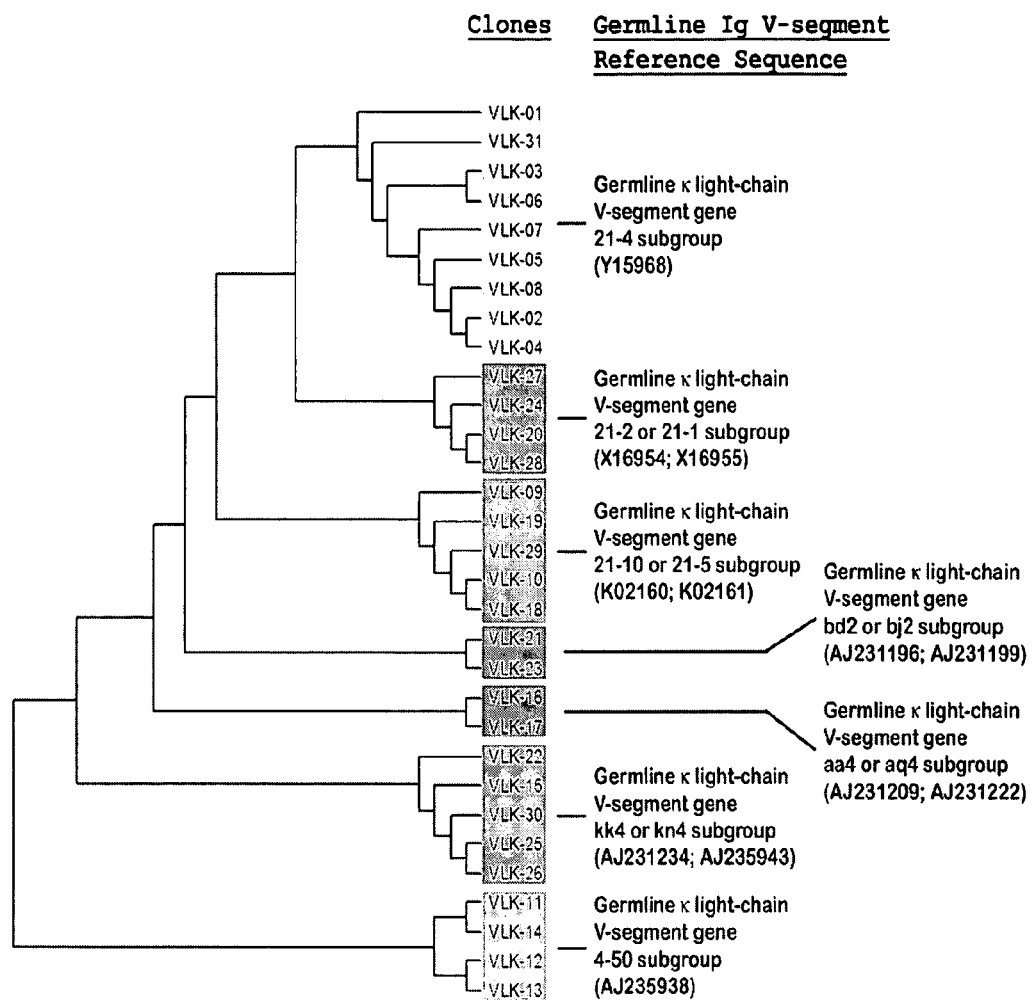
FIGS. 3A and 3B show cladogram of sequencing analysis of kapa-light (3A) and heavy (3B) chain variable region of Ig genes from non-immunized mouse splenocytic genomic DNA. The difference between the most related gene sequence is 23.6% and 62.3% for $V_{L-\kappa}$ and $V_H$, respectively.

As described above, the present invention provides a method for preparing an antigen-specific antibody by constructing a library of a phage-displayed single chain variable fragment (ScFv) of an antibody using a novel frame-shifting PCR.

In the procedure of the frame-shifting PCR, diverse Ig genes ($V_{L-\kappa}$ or $V_H$ genes) of variable lengths and sequences are generated within the CDR3 region, so that defective Ig genes resulted from non-productive exon joining are recovered to hereby enhance the diversity in the CDR3 region. As shown in FIG. 1, Ig genes variable regions derived by a semi-nested PCR were served as template for the frame-shifting PCR which allows reverse primers sliding along the CDR3 region of the Ig gene variable regions. After the frame-shifting PCR modification, a library of the Ig variable regions with different lengths and sequences within the CDR3 region has been generated.

The semi-nested PCR and the frame-shifting PCR mentioned above are performed using a set of degenerated primers which cover most of Ig genes. According to the invention, a PCR primer (or, an oligonucleotide primer) is an oligonucleotide capable of specific hybridization under particular PCR conditions to a region of the template DNA. Each primer is typically used as a member of a primer pair, including a 5' upstream primer that hybridizes with the 5' end of the template DNA to be amplified and a 3' downstream primer that hybridizes with the complement of the 3' end of the template DNA to be amplified. Those skilled in the art to which the invention relates will understand primers useful in connection with the present invention may be prepared by any conventional DNA synthesis methods.

In the method for constructing a library of the $V_{L-\kappa}$ or $V_H$ genes, the $V_{L-\kappa}$ or $V_H$ gene fragments retrieved are cloned into a vector to construct the library. The vector used in the invention can be any vectors that conveniently express the genes in a host cell, including, but not limited to, bacterial plasmid vectors selected from expression, cloning, cosmid and transformation vectors such as pBR322, and animal viral vectors such as modified adenovirus, influenza virus, adeno-associated virus, polio virus, pox virus, retrovirus, and the like. Detecting and screening the library are performed by any of technology known to ordinary skill persons in the art.

In the method for constructing a mammalian single-chain variable region (ScFv) phage-displayed library, both an adaptor and a linker are introduced to the frame-shifted immunoglobulin gene variable regions. Then the heavy and κ/λ-light chains ($V_H$ & $V_{L-\kappa}$) are linked so that the single-chain variable region (ScFv) is constructed. In one embodiment of the invention, the above procedure is carried out by two PCRs. That is the first PCR is an ordinary one and the second PCR is an overlap-extensive PCR. The resulted products are then cloned into a vector to constitute the library.

The present invention breaks through the limitation that using mRNA as an enriched source of expressed and spliced antibody genes neglects the allelic exclusive genes so as half of the potential gene by retrieving Ig genes from a germline DNA. A supplementary PCR strategy ("frame-shifting PCR") introduces diversity into the CDR3 region of immunoglobulin so as to recover defective Ig genes resulted from non-productive exon joining and further to enhance the diversity in the CDR3 region. The method provided by the present invention for preparing antigen-specific antibody has been evaluated by construction of a small ScFv phage display library. Furthermore, ELISA and competitive phageELISA indicated significant differences in affinity among different clones.

A fast and simple method for retrieving the variable region of Ig genes and simultaneously introducing sequence diversity in the CDR3 region of antigen recognition domain is provided by the present invention.

It is understood that the antigen-specific monoclonal antibody prepared by the method of the present invention can be applied to prevent, diagnose and treat diseases of mammalians related to infection of the specific antigen, and to a kit containing the antibody.

The present invention will be further described with the following examples in conjunction with the drawings.

EXAMPLES

Example 1

Construction of Libraries of $V_{L-\kappa}$ or $V_H$ Genes

Primers Used in the Examples

Primers used for amplification reactions were listed as follows:

```
A. Mouse V_H Forward Primers (FR1 Region):
F1:    5'- gAggTgMWgcTKVWg                                        (SEQ ID NO:194)
F2:    5'- gAggTgMWgcTKVWgSAgTcTggA                               (SEQ ID NO:195)
SBS1:  5'- cgAgcTcggATccggcccAgccggccSAggTgMWgcTKVWgSAg           (SEQ ID NO:196)

B. Mouse V_H Reverse Primers (FR4 Region):
R1:    5'- gAcDgTgASHRDRgT                                        (SEQ ID NO:197)
R2:    5'- gAcDgTgASHRDRgTBccTKSRccccA                            (SEQ ID NO:198)
R3:    5'- gAcDgTgASHRDRgTBccTKSRccccANNNNNN                      (SEQ ID NO:199)
L1JP:  5'- AgAAccgcTgccTgAAccgccTccAccAcTgAcDgTgASHRDRgTBccT      (SEQ ID NO:200)
```

-continued

C. Mouse V$_{L-\kappa}$ Forward Primers (FR1 Region):
```
F11:    5'- gAHRTYgTKMTSAc                                    (SEQ ID NO:201)
F12:    5'- gAHRTYgTKMTSAcMcARWcTMcA                          (SEQ ID NO:202)
L2JP:   5'- TcAggcAgcggTTcTAgcggcggTggcggAgAHRTYgTKMTSAcMcARWc (SEQ ID NO:203)
```

D. Mouse V$_{L-\kappa}$ Reverse Primers (FR4 Region):
```
R11:    5'- KATYTccARYYTKgT                                   (SEQ ID NO:204)
R12:    5'- KATYTccARYYTKgTSccHBcDccgAA                       (SEQ ID NO:205)
R13:    5'- YYTKgTSccHBcDccgAAYgTNNNNNN                       (SEQ ID NO:206)
KN1:    5'- cggggTAccgcggccgcKATYTccARYYTKgTSccHBcDccgAA      (SEQ ID NO:207)
```

E. Mouse V$_{L-\lambda}$ Forward Primers (FR1 Region):
```
F21:    5'- cAggcTgTTgTgA                                     (SEQ ID NO:208)
F22:    5'- cAggcTgTTgTgAcTcAggAATcT                          (SEQ ID NO:209)
L3JP:   5'- TcAggcAgcggTTcTAgcggcggTggcggAcAggcTgTTgTgAcTc    (SEQ ID NO:210)
```

F. Mouse V$_{L-\lambda}$ Reverse Primers (FR4 Region):
```
R21:    5'- AccTAggAcAgTcA                                    (SEQ ID NO:211)
R22:    5'- AccTAggAcAgTcAVYYTggTTcc                          (SEQ ID NO:212)
R23:    5'- AgTcAVYYTggTTccWcTNcMgAAMAYNNNNNN                 (SEQ ID NO:213)
KN2:    5'- cgggTAccgcggccgcAgTcAVYYTggTTccWcYNcMgAA          (SEQ ID NO:214)
```

Amiplifying Genomic DNAs Extracted from Lymphocytes

The CD19$^+$ lymphocytes were isolated from spleen of a non-immunized Balb/C mouse. Genomic DNA was extract by use of DNAzol Reagent (Cat #: 10503-027) from GibcoBRL Life Technology with procedures as detailed by the manufacturer. Particularly, 1 ml of DNAzol reagent was added to splenocytic lymphocytes ($10^7$) and cells were lysed by gently pipetting up and down. The cell lysate was centrifugated for 10 minutes at 10,000 g at 4° C. After centrifugation, the viscous supernatant was transferred to a new tube. DNA was precipitated by adding 0.5 ml of 100% ethanol per ml of DNAzol used. The sample was mixed by inversion and then incubated at room temperature for 3 minutes. The cloudy DNA precipitate was removed from tube by spooling with a pipette tip and then transferred to a new tube. After washing twice with 1 ml of 75% ethanol, the DNA precipitate was air-dried and then re-dissolved in distilled water for next used.

A mixture containing the following components was used to amplify the Ig gene variable region from the genomic DNA.

| Name | V$_H$ Vol. (μl) | V$_{L-\kappa}$ Vol. (μl) | Final Conc. |
|---|---|---|---|
| 1) 10X PCR buffer | 5 | 5 | 1X |
| 2) 25 mM MgCl$_2$ | 3 | 3 | 1.5 mM |
| 3) 10 mM dNTP | 1 | 1 | 0.2 mM |
| 4) 10 μM F1 V$_H$ primer | 1.5 | — | 0.3 μM |
| 5) 10 μM R1 V$_H$ primer | 6.5 | — | 1.3 μM |
| 6) 10 μM F11 V$_{L-k}$ primer | — | 2.25 | 0.45 μM |
| 7) 10 μM R11 V$_{L-k}$ primer | — | 1.5 | 0.3 μM |
| 8) 100% DMSO | 2.5 | 2.5 | 5% |
| 9) Splenocytic genomic DNA | x | x | 100 ng/50 μl |
| 10) 5 U/μl Taq. Polymerase | 0.5 | 0.5 | 0.05 U/μl |
| 11) Sterilized H$_2$O | x | x | make up to 50 μl |
| Total | 50 | 50 | (μl) |

PCR condition: 30 cycles (~1.5 hr)

For both V$_H$ and V$_{L-\kappa}$:

| Preheating | Denaturation | Annealing | Extension | Post-extension | Storage |
|---|---|---|---|---|---|
| 94° C. 45 sec. | 94° C. 15 sec. | 40° C. 1.5 min. | — | — | 4° C. infinity |

Products of the amplification reaction were analyzed by agarose gel electrophoresis. The result was shown in FIG. 2. The PCR product of genomic DNA amplification with primer pair for heavy chain of Ig genes was shown in lane 1.

Recovering Variable Regions of Ig Heavy and κ-Light Chains by Semi-Nested PCR

The PCR product of the first round PCR amplification of V$_H$ and V$_{L-\kappa}$ were used as templates for the 2nd round semi-nested PCR of Ig heavy and κ-light chains, respectively. A mixture used in the amplification included:

| Name | V$_H$ Vol. (μl) | V$_{L-\kappa}$ Vol. (μl) | Final Conc. |
|---|---|---|---|
| 1) 10X PCR buffer | 5 | 5 | 1X |
| 2) 25 mM MgCl$_2$ | 3 | 3 | 1.5 mM |
| 3) 10 mM dNTP | 1 | 1 | 0.2 mM |
| 4) 10 μM F2 V$_H$ primer | 1.5 | — | 0.3 μM |
| 5) 10 μM R2 V$_H$ primer | 7.5 | — | 1.5 μM |
| 6) 10 μM F12 V$_{Lk}$ primer | — | 2.5 | 0.5 μM |
| 7) 10 μM R12 V$_{Lk}$ primer | — | 5.6 | 1.12 μM |
| 8) 100% DMSO | 2.5 | 2.5 | 5% |
| 9) 1$^{st}$ PCR mixture, (V$_H$/V$_{Lk}$) | 3 | 3 | (μl) |
| 10) 5 U/μl Taq. Polymerase | 0.5 | 0.5 | 0.05 U/μl |
| 11) Sterilized H$_2$O | 26 | 26.9 | make up to 50 μl |
| Total | 50 | 50 | (μl) |

PCR condition: 35 cycles and

For $V_H$:

| Preheating | Denaturation | Annealing | Extension | Post-extension | Storage |
|---|---|---|---|---|---|
| 94° C. 2 min. | 94° C. 30 sec. | 65° C. 40 sec. | — | 65° C. 2 min. | 4° C. infinity |

For $V_{L-\kappa}$:

| Preheating | Denaturation | Annealing | Extension | Post-extension | Storage |
|---|---|---|---|---|---|
| 94° C. 2 min. | 94° C. 30 sec. | 58° C. 40 sec. | — | 58° C. 2 min. | 4° C. infinity |

Variable regions of immunoglobulin heavy and κ/λ-light chains ($V_H$ & $V_{L-\kappa}$) were obtained by the semi-nested PCR amplification. The PCR products were run on agarose gel with ethidium bromide staining and ultraviolet-light visualization. The result was shown in lanes 2 and 3 of FIG. 2. Following electrophoretic migration, the gel was removed and the amplified products were extracted from the gel.

Amplifying Immunoglobulin Gene Variable Regions by Frame-Shifting PCR

A frame-shifting PCR was carried out using templates of $V_H$ & $V_{L-\kappa}$ produced by the semi-nested PCR. A mixture used for the frame-shifting PCR contained the following components:

| Name | $V_H$ Vol. (μl) | $V_{L-\kappa}$ Vol. (μl) | Final Conc. |
|---|---|---|---|
| 1) 10X PCR buffer | 5 | 5 | 1X |
| 2) 25 mM MgCl$_2$ | 3 | 3 | 1.5 mM |
| 3) 10 mM dNTP | 1 | 1 | 0.2 mM |
| 4) 10 μM F1* $V_H$ primer | 2.5 | — | 0.5 μM |
| 5) 10 μM R3 $V_H$ primer | 20 | — | 4 μM |
| 6) 10 μM F12 $V_{Lk}$ primer | — | 2.5 | 0.5 μM |
| 7) 10 μM R13 $V_{Lk}$ primer | — | 20 | 4 μM |
| 8) Gel-extracted semi-nested PCR pdt. (sn$V_H$/sn$V_{Lk}$) | x | x | 60 ng/50 μl |
| 9) 5 U/μl Taq. Polymerase | 0.5 | 0.5 | 0.05 U/μl |
| 10) Sterilized H$_2$O | x | x | make up to 50 μl |
| Total | 50 | 50 | (μl) |

PCR condition: 25 cycles (Overnight: ~8 hrs) and

For both $V_H$ and $V_{L-\kappa}$:

| Preheating | Denaturation | Annealing | Extension | Post-extension | Storage |
|---|---|---|---|---|---|
| 94° C. 2 min. | 94° C. 30 sec. | 20° C. 2 min. | ramping up w/speed 0.1° C./sec. | — | 4° C. infinity |

The amplified products were analyzed by agarose gel electrophoresis (FIG. 2, lane 4). In the procedure of the frame-shifting PCR, diverse Ig genes ($V_{L-\kappa}$ or $V_H$ genes) of variable lengths and sequences within the CDR3 region were generated. As a result, diversity was introduced into the CDR3 region of the immunoglobulin genes so that defective Ig genes resulted from non-productive exon joining were recovered to hereby enhance the diversity in the CDR3 region as shown in FIG. 1.

Transformation and Sequencing Analysis

Libraries of $V_H$ and $V_{L-\kappa}$ variable region derived from the frame-shifting PCR were cloned into TOPO TA vector. Particularly, ligation mixture was used to transform TG1 or DH5α E. coli cells either by standard calcium chloride-mediated transformation, or by electroporation at 1900 V/cm, resistance at 200Ω, and the capacitance at 50 μF with 0.1 cm electroporation cuvettes and a Bio-Rad electroporator. Transformed competent cells were plated on agar plates containing ampicillin (100 ug/ml) and incubated at 37° C. overnight. Transformed colonies were randomly picked from the agar plates. Plasmid DNA was prepared from overnight bacterial culture by use of QIAprep Spin Miniprep kit (Qiagen). Purified plasmid were used for sequence determination of $V_H$ and $V_{L-\kappa}$ clones by fluorescent dye-labelled terminator cycle sequencing with a Beckman CEQ 2000 autosequencer.

Figure 3B:
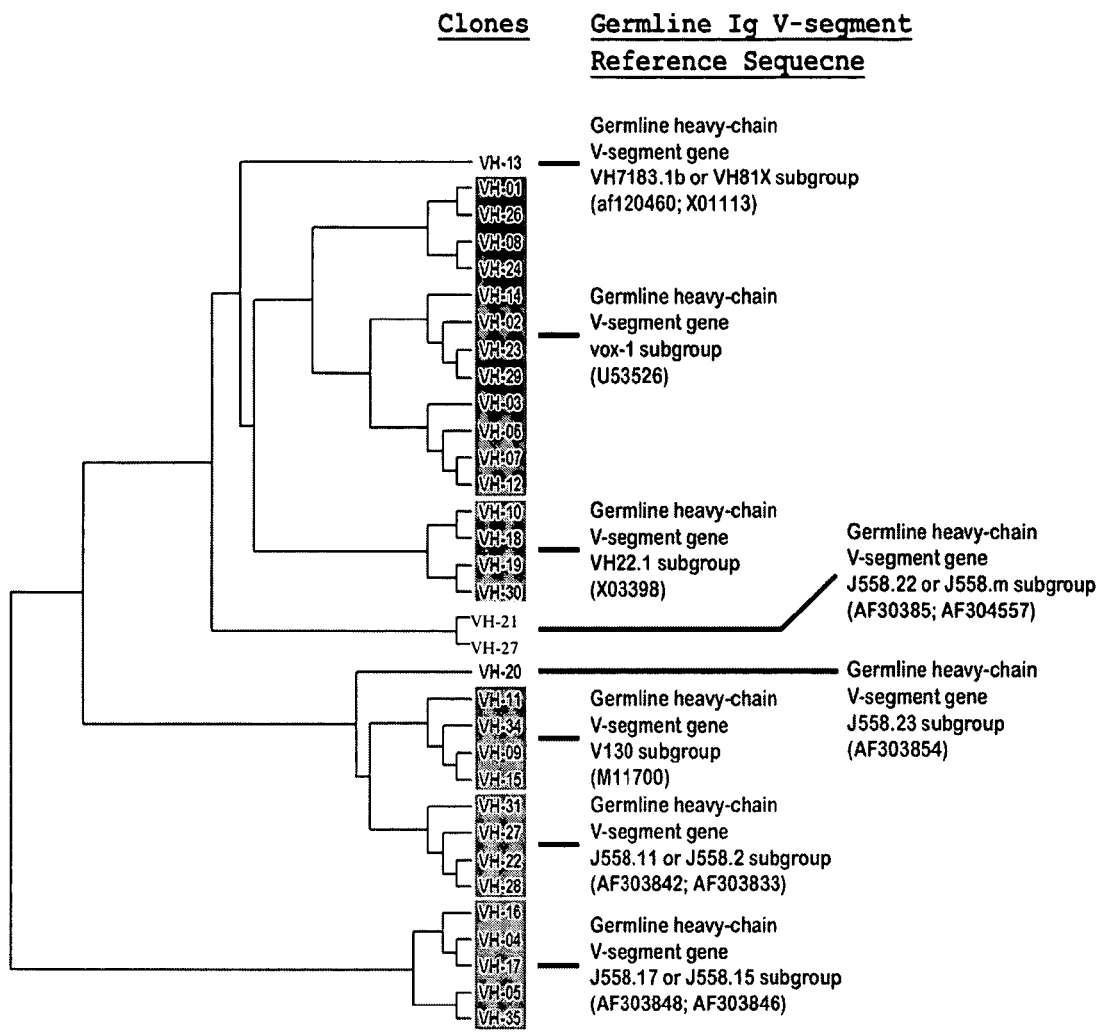
Figure 4:
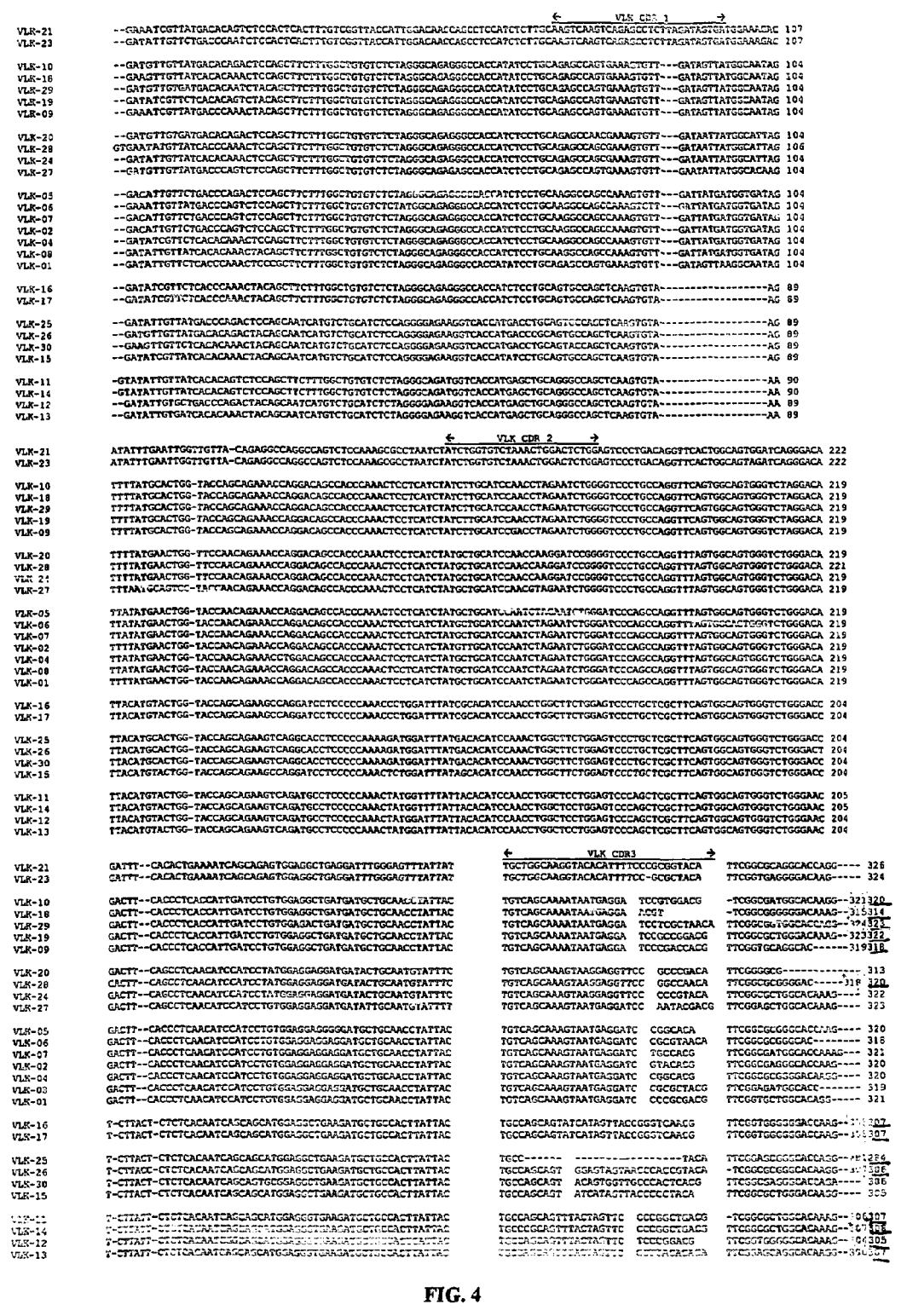

120 transformants from each library were randomly picked for sequencing analysis. Phylogenic analysis indicated that, with respect to the germline Ig sequences in NCBI database as reference sequences, the 31 and 33 full-length sequenced $V_{L-\kappa}$ or $V_H$ clones can be classified into 7 and 8 different families, respectively (FIG. 3). Moreover, multiple sequence alignments revealed that significant sequence differences within the CDR3 region among those sequenced clones (FIG. 4).

In this experiment, we aimed at providing proof-of-concept evidence for frame-shifting PCR. Specifically two questions were addressed: (1) non-immunised genomic DNA can be used as template for construction of immunoglobulin chain library by frame-shifting PCR; (2) application of frame-shifting PCR would generate an immunoglobulin chain-library consisting of heterogeneous Ig sequences with significant diversity in the CDR3 region (FIG. 1). As illustrated in FIG. 2, variable region of immunoglobulin chains in the genomic DNA can be efficiently recovered by the semi-nest PCR steps though present in minutes amount (FIG. 2, lane 1–lane 2). With the use of gel-purified ~340-bp PCR product of semi-nest PCR (FIG. 2, lane 3) as a template, frame-shifting PCR generates a library of DNA segments that is heterogeneous in size (FIG. 2, lane 4). Following TA-cloning, the nucleotide sequence of frame-shifting PCR products was determined. To analyze the diversity of the immunoglobulin chain libraries, full-length sequences of randomly picked clones of a library were subjected to phylogeny analysis with a web-based software (ClustalW of European Bioinformatics Institute). As indicated in FIG. 3, clones can be grouped into different families, suggesting the library consisting of heterogeneous immunoglobulin chains. Furthermore, to evaluate whether frame-shifting PCR enhances CDR3 diversity as predicted (FIG. 1), clones of the $V_{L-\kappa}$ library were subjected to multiple sequences alignment. As shown in FIG. 4, clones of each family are mostly identical except notable sequence difference in the CDR3 region. The result suggests that clones of each family might be derived from a single template, and diversity is introduced into the CDR3 region by frame-shifting PCR.

Example 2

Construction of Single Chain Variable Antibody Fragment (scFv)

Construction of Libraries of $V_{L\kappa}$ and $V_H$ Genes

Libraries of $V_{L\kappa}$ and $V_H$ Genes were constructed as described in Example 1, except the CD19+ lymphocytes were isolated from spleen of a Balb/C mouse that was immunised with 4-ethoxymethylene-2-phenyl-2-oxazolin-5-one (phOx) conjugated to chicken serum albumin (CSA, Sigma, USA).

Construction of Single Chain Variable Antibody Fragment (ScFv)

Both an adaptor and a linker were introduced into the frame-shifted immunoglobulin gene variable regions by PCR using a reactive mixture including the following components:

| Name | $V_H$ Vol. (µl) | $V_{L-\kappa}$ Vol. (µl) | Final Conc. |
|---|---|---|---|
| 1) 10X PCR buffer | 5 | 5 | 1X |
| 2) 25 mM MgCl$_2$ | 3 | 3 | 1.5 mM |
| 3) 10 mM dNTP | 1 | 1 | 0.2 mM |
| 4) 10 µM SBS1 $V_H$ adaptor | 1 | — | 0.2 µM |
| 5) 10 µM L1JP $V_H$ Linker | 1 | — | 0.2 µM |
| 6) 10 µM L2JP $V_{Lk}$ Linker | — | 1 | 0.2 µM |
| 7) 10 µM KN1 $V_{Lk}$ adaptor | — | 1 | 0.2 µM |
| 8) 100% DMSO | 2.5 | 2.5 | 5% |
| 9) Gel-extracted frame-shifted PCR pdt. (fsV$_H$ or fsV$_{Lk}$) | x | x | 60 ng/50 µl |
| 10) 5 U/µl Taq. Polymerase | 0.5 | 0.5 | 0.05 U/µl |
| 11) Sterilized H$_2$O | x | x | make up to 50 µl |
| Total | 50 | 50 | (µl) |

PCR condition: 15 cycles (~1 hr) and for both $V_H$ and $V_{L-\kappa}$:

| Preheating | Denaturation | Annealing | Extension | Post-extension | Storage |
|---|---|---|---|---|---|
| 94° C. 2 min. | 94° C. 30 sec. | 54° C. 30 sec. | 72° C. 30 sec. | 72° C. 2 min. | 4° C. infinity |

A resultant product followed an overlap-extensive PCR to construct single-chain variable regions in which the $V_H$ gene with an adaptor and a linker was connected to the $V_{L-\kappa}$ gene with a linker and an adaptor. A mixture used for overlap-extensive PCR comprised the following components.

| Name | ScFv Vol. (µl) | Final Conc. |
|---|---|---|
| 1) 10X PCR buffer | 5 | 1X |
| 2) 25 mM Mg$_2$Cl | 3 | 1.5 mM |
| 3) 10 mM dNTP | 1 | 0.2 mM |
| 4) 10 µM SBS1 $V_H$ adaptor | 1 | 0.2 µM |
| 5) 10 µM KN1 $V_{Lk}$ adaptor | 1 | 0.2 µM |
| 6) 100% DMSO | 2.5 | 5% |
| 7) Adaptor linked fsV$_H$ | 5 | (PCR product) |
| 8) Adaptor linked fsV$_{Lk}$ | 5 | (PCR product) |
| 9) 5 U/µl Taq. Polymerase | 0.5 | 0.05 U/µl |
| 10) Sterilized H$_2$O | 26 | make up to 50 µl |
| Total | 50 | (µl) |

PCR condition: 20 cycles (~1 hr) and

| Preheating | Denaturation | Annealing | Extension | Post-extension | Storage |
|---|---|---|---|---|---|
| 94° C. 2 min. | 94° C. 30 sec. | 58° C. 30 sec. | 72° C. 30 sec. | 72° C. 2 min. | 4° C. infinity |

Transformation, Identification and Analysis

The single-chain variable regions produced were separated by agarose gel electrophoresis and potential candidates cloned into the pCANTAB 5E phagemid vector (Amersham Pharmacia Biotech Inc.) and rescued phage clones were selected against EM-phOx (purchased from Sigma, USA) with standard biopanning procedures. Particularly, following transformed into E. Coli TG1 cells, phage clones displaying the ScFv antibody as surface ScFv-g3 fusion proteins were rescued from the transformed TG1 cells with M13KO7 helper phage. To select phage clones that are selectively bound to phOx, rescued phage clones were incubated in a 24-well tissue culture plate (0.5 ml/well) that was coated with phOx conjugated to bovine serum albumin (BSA) for 2 hours at room temperature. After removing unbound phage by washing 5 times with 2 ml/well of phosphate-buffered saline (PBS) and then 10 times with 2.5 ml/well of PBS containing 0.1% Tween-20. Bound phage clones were eluted by adding 100 ul of 0.1M glycine-HCl (pH=2.2) and incubated for 10 minutes at room temperature. Eluted clones were collected, neutralized by adding 10 ul of 1M Tris-HCl (pH=8.0). Pooled phage clones were then used to re-infect TG1 cells. Enriched phage clones were then rescued from transformed TG1 cells with M13KO7 helper phage. The biopanning cycle was repeated 5 times, and then individual phage clones were isolated.

Figure 5:
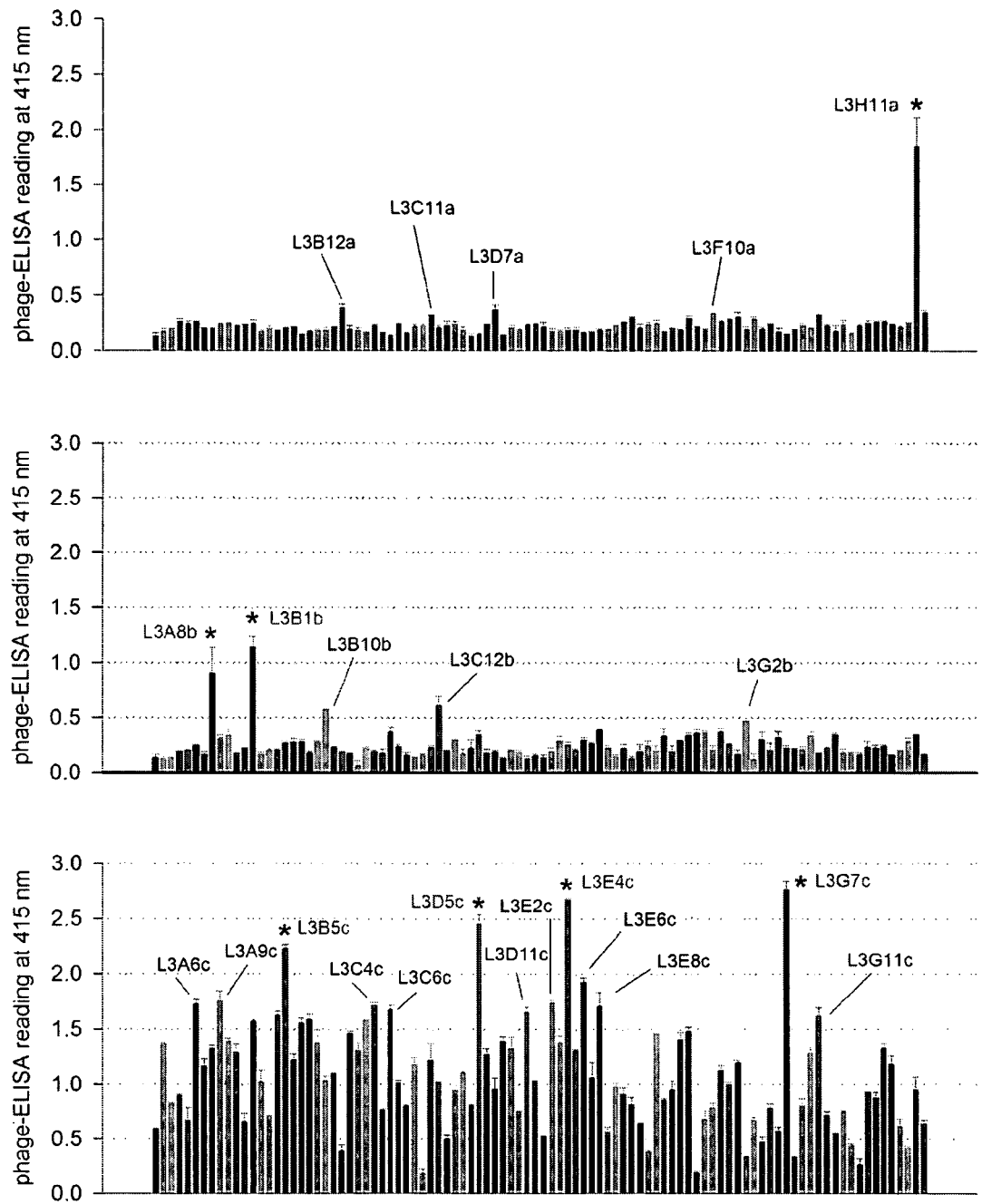
FIG. 5 shows phageELISA of candidate ScFv clones obtained after five rounds of panning against phOx-BSA conjugate (partly). ScFv clones with phageELISA reading more than 1.5 fold of the mean value of the sample set are isolated and subjected to further analysis. ScFv clones that are used for competitive phageELISA (FIG. 7) are marked with asterisks.

After 5 rounds of panning against phOx conjugated to bovine serum albumin (BSA), potential candidate clones ($9.7 \times 10^5$ recombinants) were identified. 288 Clones were randomly picked and their reactivities against phOx were determined by phageELISA. Forty-four highly reactive clones, of which reactivity towards EM-phOx were 1.5-fold higher than the mean value of the sample set, were isolated and further analyzed (FIG. 5). Phylogenic analysis of the sequences suggested that the derived Ig genes could be grouped into different classes and significant sequence variations were found within the CDR3 region of Ig genes in each class (FIG. 6). Furthermore, with the use of phOx as free ligand, competitive phageELISA indicated significant differences in affinity among different clones (FIG. 7).

Figure 7A:
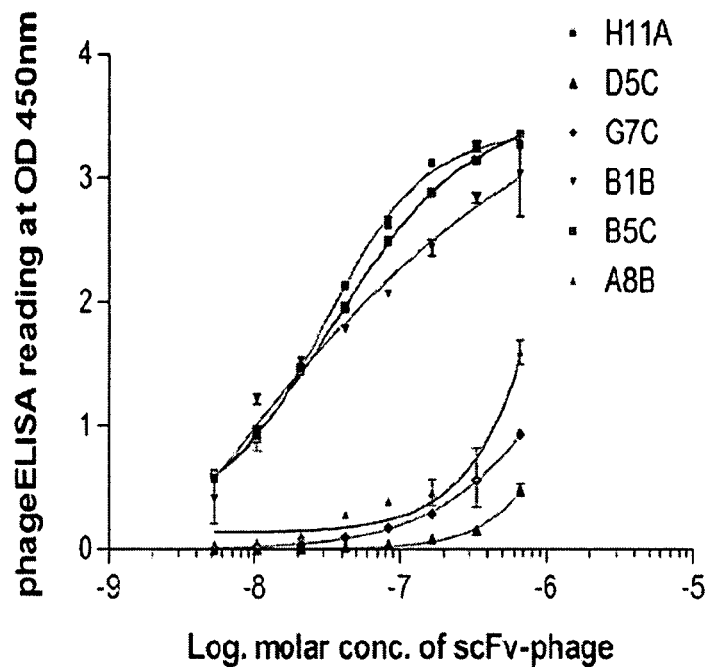
Figure 7B:
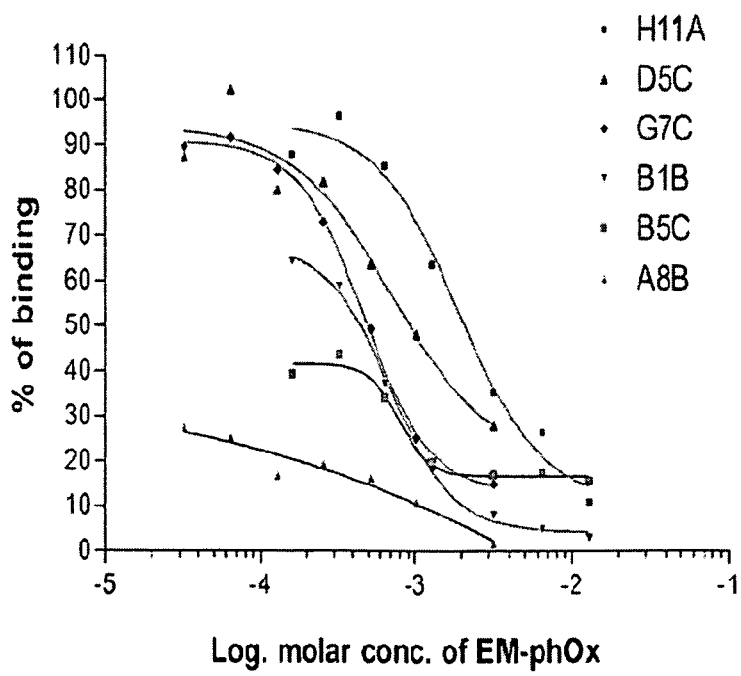

In this experiment, we aimed at testing the feasibility of using frame-shifting PCR to prepare target specific scFv antibodies. Specifically, with the use of a small molecule phenyloxazolone as a model antigen, we have prepared an scFv library by using genomic DNA that derived from CD19+ lymphocytes of an immunized Balb/C mouse as template for frame-shifting PCR. For screening scFv antibodies that selectively reacted with phOx, we expressed the scFv library as a phage-display scFv library, and then biopanning against immobilized phOx. Isolated individual phage clone was then used as a primary antibody for testing its reactivity towards phOx by an ELISA (phageELISA). A typical result of the phageELISA assay was shown in FIG. 5, and phage clones that gave high reactivity towards phOx were then further subjected for nucleotide sequence determination. Alignment of the sequences showed that the isolated phOx-specific scFv clones displayed significant sequence variation in the CDR3 region (FIG. 6), suggesting that frame-shifting PCR is capable to generate and to retrieve heterogeneous functional scFv antibodies. On the other hand, it is predicted that a highly diverse antibody library should consist of scFv clones displaying a wide range of affinity toward antigens. Hence we compared the affinity of the isolated phOx-specific scFv clones by saturation analysis with phageELISA (FIG. 7A), and by a competitive phageELISA in which free phOx was used to compete with immobilized phOx for binding to the isolated scFv clones (FIG. 7B). Indeed, isolated phOx-specific phage clones bound to immobilized phOx in a concentration-dependent manner, with affinity (EC50) approximately spanning one and a half log scale amongst different scFv clones (FIG. 7A). In agreement with saturation analysis, binding of scFv towards immobilized phOx were concentration-dependently displayed by free phOx, and the IC50 value of various scFv clones approximately spanning through two log scale (FIG. 7B). These results imply that frame-shifting PCR produces highly diverse scFv library consisting of target-specific scFv antibodies characterized with a wide spectrum of affinities.

What is claimed is:

1. A method for preparing single-chain variable fragments encoding an antigen-specific antibody, comprising the steps of:
   a) extracting genomic DNAs of lymphocytes from a non-immunized mammal or a mammal immunized with a specific antigen;
   b) recovering variable regions of immunoglobulin heavy and light chains from the genomic DNAs;
   c) amplifying the variable regions using PCR with a forward primer and a set of different reverse primers designed for the variable regions, wherein the reverse primers are represented by gAcDgTgASHRDRgTBc-cTKSRccccANNNNNN for $V_H$ or YYTKgTSccHB-cDccgAAYgTNNNNNN for $V_{L\text{-}\kappa}$, in which N is A, c, T or g, R is A or g, Y is c or T, M is A or c, K is T or g, S is c or g, H is A, T or c, B is T, c or g, and D is A, T or g;

d) introducing both an adaptor and a linker to the variable regions obtained in step c); and e) linking the variable regions obtained in step d) by an overlap-extensive PCR to obtain single-chain variable fragments.

2. The method of claim 1, wherein the step b) is performed by a semi-nested PCR.

3. The method of claim 2, wherein the mammal is a mouse.

4. The method of claim 2, wherein the specific antigen is 4-ethoxymethylene-2-phenyl-2-oxazolin-5-one conjugated to chicken serum albumin.

5. The method of claim 1, wherein the forward primer is gAggTgMWgcTKVWg for $V_H$, in which M is A or c, K is T or g, W is A or T, and V is A, c or g.

6. The method of claim 1, wherein the forward primer is gAHRTYgTKMTSAcMcARWcTMcA for $V_{L-\kappa}$, in which R is A or g, Y is c or T, M is A or c, K is T or g, S is c or g, and H is A, T or c.

7. The method of claim 1, wherein the PCR for both VH and VL-$\kappa$ is performed with a condition as follows:
preheating at 94° C. for 2 min, then followed with 25 cycles of denaturation at 94° C. for 30 sec, annealing at 20° C. for 2 min, extension at ramping up w/speed 0.1° C./sec, and then storage at 4° C.

8. The method of claim 1, wherein the lymphocytes are splenoctic CD$^+$19 cells.

9. A method for preparing an antigen-specific antibody comprising:

a) extracting lymphocytic genomic DNAs from a non-immunized mammal or a mammal immunized with a specific antigen;

b) recovering variable regions of immunoglobulin heavy and light chains from the genomic DNAs;

c) amplifying the variable regions using PCR with a forward primer and a set of different reverse primers designed for the variable regions, wherein the reverse primers are represented by gAcDgTgASHRDRgTBccTKSRccccANNNNNN for $V_H$ or YYTKgTSccHBcDccgAAYgTNNNNNN for $V_{L-\kappa}$, in which N is A, c, T or g, R is A or g, Y is c or T, M is A or c, K is T or g, S is c or g, H is A, T or c, B is T, c or g, and D is A, T or g;

d) introducing both an adaptor and a linker to the variable regions obtained in step c);

e) linking the variable regions obtained in step d) by an overlap-extensive PCR to construct single-chain variable fragments; and f) introducing the single-chain variable fragments into a host cell and expressing the cell.

10. The method of claim 9, wherein the antigen-specific antibody is a monoclonal antibody.

11. The method of claim 10, wherein the monoclonal antibody is a monoclonal antibody of single-chain variable fragments.

12. A method for retrieving either $V_{L-\kappa}$ or $V_H$ genes from a genomic DNA comprising the steps of:

a) extracting lymphocytic genomic DNAs from a mammal;

b) recovering variable regions of immunoglobulin heavy and light chains from the genomic DNAs using a semi-nested PCR; and c) amplifying the variable regions using PCR to produce $V_{L-\kappa}$ or $V_H$ genes of variable lengths or sequences, with a set of different reverse primers which are represented by gAcDgTgASHRDRgTBccTKSRccccANNNNNN for $V_H$ or YYTKgTSccHBcDccgAAYgTNNNNNN for $V_{L-\kappa}$, in which N is A, c, T or g, R is A or g, Y is c or T, M is A or c, K is T or g, S is c or g, H is A, T or c, B is T, c or g, and D is A, T or g.

13. The method of claim 12, wherein the mammal is a non-immunized one or immunized with a specific antigen.

14. The method of claim 13, wherein the mammal is a mouse and the specific antigen is 4-ethoxymethylene-2-phenyl-2-oxazolin-5-one conjugated to chicken serum albumin.

15. A method for constructing a library of recombinant nucleotide sequences encoding $V_{L-\kappa}$ or $V_H$ genes from a genomic DNA comprising the steps of:

a) extracting lymphocytic genomic DNAs from a mammal;

b) recovering variable regions of immunoglobulin heavy and light chains from the genomic DNAs using a semi-nested PCR;

c) amplifying the variable regions using PCR to produce $V_{L-\kappa}$ or $V_H$ genes of variable lengths or sequences, with a set of different reverse primers which are represented by gAcDgTgASHRDRgTBccTKSRccccANNNNNN for $V_H$ or YYTKgTSccHBcDccgAAYgTNNNNNN for $V_{L-\kappa}$, in which N is A, c, T or g, R is A or g, Y is c or T, M is A or c, K is T or g, S is c or g, H is A, T or c, B is T, c or g, and D is A, T or g; and d) cloning the $V_{L-\kappa}$ or $V_H$ genes into a vector.

16. The method of claim 15, wherein the mammal is a non-immunized one or immunized with a specific antigen.

17. The method of claim 16, wherein the mammal is mouse and the specific antigen is 4-ethoxymethylene-2-phenyl-2-oxazolin-5-one conjugated to chicken serum albumin.

18. The method of claim 15, wherein the vector is a TOPO TA vector.

19. The method of claim 17, wherein the vector is a TOPO TA vector.

* * * * *

SEQUENCE LISTING

<160> NUMBER OF SEQ ID NOS: 214

<210> SEQ ID NO 1
<211> LENGTH: 326
<212> TYPE: DNA
<213> ORGANISM: Mus musculus

<400> SEQUENCE: 1

```
gaaatcgtta tgacacagtc tccactcact ttgtcggtta ccattggaca accagcctcc      60
atctcttgca agtcaagtca gagcctctta gatagtgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acattttccc     300
gcggtacatt cggcgcaggc accagg                                          326
```

<210> SEQ ID NO 2
<211> LENGTH: 324
<212> TYPE: DNA
<213> ORGANISM: Mus musculus

<400> SEQUENCE: 2

```
gatattgttc tgacccaatc tccactcact ttgtcggtta ccattggaca accagcctcc      60
atctcttgca agtcaagtca gagcctctta gatagtgatg gaaagacata tttgaattgg     120
ttgttacaga ggccaggcca gtctccaaag cgcctaatct atctggtgtc taaactggac     180
tctggagtcc ctgacaggtt cactggcagt agatcaggga cagatttcac actgaaaatc     240
agcagagtgg aggctgagga tttgggagtt tattattgct ggcaaggtac acattttccg     300
cgctacattc ggtgagggga caag                                            324
```

<210> SEQ ID NO 3
<211> LENGTH: 320
<212> TYPE: DNA
<213> ORGANISM: Mus musculus

<400> SEQUENCE: 3

```
gatgttgtta tgacacagac tccagcttct ttggctgtgt ctctagggca gagggccacc      60
atatcctgca gagccagtga aagtgttgat agttatggca atagtttat gcactggtac     120 cagcagaaac aggacagcc acccaaactc ctcatctatc ttgcatccaa cctagaatct     180
ggggtccctg ccaggttcag tggcagtggg tctaggacag acttcaccct caccattgat     240
cctgtggagg ctgatgatgc tgcaacctat tactgtcagc aaaataatga ggatccgtgg     300
acgtcggcga tggcacaagg                                                 320
```

```
<210> SEQ ID NO 4
<211> LENGTH: 314
<212> TYPE: DNA
<213> ORGANISM: Mus musculus

<400> SEQUENCE: 4
gaagttgtta tcacacaaac tccagcttct ttggctgtgt ctctagggca gagggccacc        60
atatcctgca gagccagtga agtgttgat agttatggca atagttttat gcactggtac       120
cagcagaaac caggacagcc acccaaactc ctcatctatc ttgcatccaa cctagaatct      180
ggggtccctg ccaggttcag tggcagtggg tctaggacag acttcaccct caccattgat     240
cctgtggagg ctgatgatgc tgcaacctat tactgtcagc aaaataatga ggaacgttcg    300 gcgggggggac aaag                                                         314

<210> SEQ ID NO 5
<211> LENGTH: 323
<212> TYPE: DNA
<213> ORGANISM: Mus musculus

<400> SEQUENCE: 5
gatgttgtga tgacacaatc tacagcttct ttggctgtgt ctctagggca gagggccacc       60
atatcctgca gagccagtga agtgttgat agttatggca atagttttat gcactggtac       120
cagcagaaac caggacagcc acccaaactc ctcatctatc ttgcatccaa cctagaatct      180
ggggtccctg ccaggttcag tggcagtggg tctaggacag acttcaccct caccattgat     240
cctgtggaga ctgatgatgc tgcaacctat tactgtcagc aaaataatga ggatcctcgc    300
taacattcgg cggtggcacc agg                                                323

<210> SEQ ID NO 6
<211> LENGTH: 322
<212> TYPE: DNA
<213> ORGANISM: Mus musculus

<400> SEQUENCE: 6
gatatcgttc tcacacagtc tacagcttct ttggctgtgt ctctagggca gagggccacc       60
atatcctgca gagccagtga agtgttgat agttatggca atagttttat gcactggtac       120
cagcagaaac caggacagcc acccaaactc ctcatctatc ttgcatccaa cctagaatct      180
ggggtccctg ccaggttcag tggcagtggg tctaggacag acttcaccct caccattgat     240
cctgtggagg ctgatgatgc tgcaacctat tactgtcagc aaaataatga ggatccgccg    300
gacgttcggc gctgggacaa ag                                                 322

<210> SEQ ID NO 7
<211> LENGTH: 318
<212> TYPE: DNA
<213> ORGANISM: Mus musculus

<400> SEQUENCE: 7
gaaatcgtta tgacccaaac tacagcttct ttggctgtgt ctctagggca gagggccacc       60
atatcctgca gagccagtga agtgttgat agttatggca atagttttat gcactggtac       120
cagcagaaac caggacagcc acccaaactc ctcatctatc ttgcatccga cctagaatct      180
ggggtccctg ccaggttcag tggcagtggg tctaggacag acttcaccct caccattgat     240
cctgtggagg ctgatgatgc tgcaacctat tactgtcagc aaaataatga ggatcccgac    300
cacgttcggt gcaggcac                                                      318
```

<210> SEQ ID NO 8
<211> LENGTH: 313
<212> TYPE: DNA
<213> ORGANISM: Mus musculus

<400> SEQUENCE: 8

| gatgttgtga | tgacacagac | tccagcttct | ttggctgtgt | ctctagggca | gagggccacc | 60 |
| atctcctgca | gagccaacga | aagtgttgat | aattatggca | ttagtttat | gaactggttc | 120 |
| caacagaaac | caggacagcc | acccaaactc | ctcatctatg | ctgcatccaa | ccaaggatcc | 180 |
| ggggtccctg | ccaggtttag | tggcagtggg | tctgggacag | acttcagcct | caacatccat | 240 |
| cctatggagg | aggatgatac | tgcaatgtat | ttctgtcagc | aaagtaagga | ggttccgccc | 300 |
| gacattcggg | gcg | | | | | 313 |

<210> SEQ ID NO 9
<211> LENGTH: 320
<212> TYPE: DNA
<213> ORGANISM: Mus musculus

<400> SEQUENCE: 9

| gtgaatatgt | tatcacccaa | actccagctt | ctttggctgt | gtctctaggg | cagagggcca | 60 |
| ccatctcctg | cagagccagc | gaaagtgttg | ataattatgg | cattagtttt | atgaactggt | 120 |
| tccaacagaa | accaggacag | ccacccaaac | tcctcatcta | tgctgcatcc | aaccaaggat | 180 |
| ccggggtccc | tgccaggttt | agtggcagtg | ggtctgggac | agacttcagc | ctcaacatcc | 240 |
| atcctatgga | ggaggatgat | actgcaatgt | atttctgtca | gcaaagtaag | gaggttccgg | 300 |
| ccaacattcg | gcgcggggac | | | | | 320 |

<210> SEQ ID NO 10
<211> LENGTH: 322
<212> TYPE: DNA
<213> ORGANISM: Mus musculus

<400> SEQUENCE: 10

| gatattgtta | tcacacaaac | tccagcttct | ttggctgtgt | ctctagggca | gagggccacc | 60 |
| atctcctgca | gagccagcga | aagtgttgat | aattatggca | ttagtttat | gaactggttc | 120 |
| caacagaaac | caggacagcc | acccaaactc | ctcatctatg | ctgcatccaa | ccaaggatcc | 180 |
| ggggtccctg | ccaggtttag | tggcagtggg | tctgggacag | acttcagcct | caacatccat | 240 |
| cctatggagg | aggatgatac | tgcaatgtat | ttctgtcagc | aaagtaagga | ggttccccg | 300 |
| tacattcggc | gctggcacaa | ag | | | | 322 |

<210> SEQ ID NO 11
<211> LENGTH: 323
<212> TYPE: DNA
<213> ORGANISM: Mus musculus

<400> SEQUENCE: 11

| gatgttgtta | tgacccagtc | tccagcttct | ttggctgtgt | ctctaggca | gagagccacc | 60 |
| atctcctgca | gagccagtga | aagtgttgaa | tattatggca | aagttttaat | gcagtggtac | 120 |
| caacagaaac | caggacagcc | acccaaactc | ctcatctatg | ctgcatccaa | cgtagaatct | 180 |
| ggggtccctg | ccaggtttag | tggcagtggg | tctgggacag | acttcagcct | caacatccat | 240 |
| cctgtggagg | aggatgatat | tgcaatgtat | ttttgtcagc | aaagtaatga | ggatccaata | 300 |

```
cgacgttcgg agctggcaca aag                                             323
```

<210> SEQ ID NO 12
<211> LENGTH: 320
<212> TYPE: DNA
<213> ORGANISM: Mus musculus

<400> SEQUENCE: 12

```
gacattgttc tgacccagac tccagcttct ttggctgtgt ctctagggca gagggccacc      60
atctcctgca aggccagcca agtgttgat tatgatggtg atagttatat gaactggtac      120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggggatgc tgcaacctat tactgtcagc aaagtaatga ggatccggca      300
cattcggcgc gggcaccaag                                                 320
```

<210> SEQ ID NO 13
<211> LENGTH: 318
<212> TYPE: DNA
<213> ORGANISM: Mus musculus

<400> SEQUENCE: 13

```
gaaattgtta tgacccagtc tccagcttct ttggctgtgt ctctatggca gagggccacc      60
atctcctgca aggccagcca agtgttgat tatgatggtg atagttatat gaactggtac      120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtaatga ggatccgcgt     300
aacattcggc gcgggcac                                                   318
```

<210> SEQ ID NO 14
<211> LENGTH: 321
<212> TYPE: DNA
<213> ORGANISM: Mus musculus

<400> SEQUENCE: 14

```
gacattgttc tgacccagtc tccagcttct ttggctgtgt ctctagggca gagggccacc      60
atctcctgca aggccagcca agtgttgat tatgatggtg atagttatat gaactggtac      120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtaatga ggatctgcca     300
cgttcggcga tggcaccaaa g                                               321
```

<210> SEQ ID NO 15
<211> LENGTH: 320
<212> TYPE: DNA
<213> ORGANISM: Mus musculus

<400> SEQUENCE: 15

```
gacattgttc tgacccagtc tccagcttct ttggctgtgt ctctagggca gagggccacc      60
atctcctgca aggccagcca agtgttgat tatgatggtg atagtttat gaactggtac       120
caacagaaac caggacagcc acccaaactc ctcatctatg ttgcatccaa tctagaatct     180
gggatcccag ccaggtttag tggcagtggg tctgggacag acttcaccct caacatccat     240
cctgtggagg aggaggatgc tgcaacctat tactgtcagc aaagtaatga ggatcgtaca     300
```

```
cgttcggcga gggcaccaag                                                 320

<210> SEQ ID NO 16
<211> LENGTH: 320
<212> TYPE: DNA
<213> ORGANISM: Mus musculus

<400> SEQUENCE: 16
gatatcgttc tcacacaaac tccagcttct ttggctgtgt ctctagggca gagggccacc     60
atctcctgca aggccagcca agtgttgat  tatgatggtg atagttatat gaactggtac    120
caacagaaac ctggacagcc acccaaactc ctcatctatg ctgcatccaa tctagaatct    180
gggatcccag ccaggtttag tggcagtggg tctgggacag acttcaccct caacatccat    240
cctgtggagg aggaggatgc tgcaacctat tactgtcagc aaagtaatga ggatccggca    300
cgttcggcgc ggggacaagg                                                320

<210> SEQ ID NO 17
<211> LENGTH: 319
<212> TYPE: DNA
<213> ORGANISM: Mus musculus

<400> SEQUENCE: 17
gatattgtta tcacacaaac tacagcttct ttggctgtgt ctctagggca gagggccacc     60
atctcctgca aggccagcca agtgttgat  tatgatggtg atagttatat gaactggtac    120
caacagaaac caggacagcc acccaaactc ctcatctatg ctgcatccaa tctagaatct    180
gggatcccag ccaggtttag tggcagtggg tctgggacag acttcaccct caacatccat    240
cctgtggagg aggaggatgc tgcaacctat tactgtcagc aaagtaatga ggatccgcgc    300
tacgttcgga gatggcacc                                                 319

<210> SEQ ID NO 18
<211> LENGTH: 321
<212> TYPE: DNA
<213> ORGANISM: Mus musculus

<400> SEQUENCE: 18
gatattgttc tcacccaaac tccgcttct  ttggctgtgt ctctagggca gagggccacc     60
atatcctgca gagccagtga agtgttgat  agttaaggca atagtttat  gaactggtac    120
caacagaaac caggacagcc acccaaactc ctcatctatg ctgcatccaa tctagaatct    180
gggatcccag ccaggtttag tggcagtggg tctgggacag acttcaccct caacatccat    240
cctgtggagg aggaggatgc tgcaacctat tactgtcagc aaagtaatga ggatccccgc    300
gacgttcggt gctggcacag g                                              321

<210> SEQ ID NO 19
<211> LENGTH: 307
<212> TYPE: DNA
<213> ORGANISM: Mus musculus

<400> SEQUENCE: 19
gatatcgttc tcacccaaac tacagcttct ttggctgtgt ctctagggca gagggccacc     60
atctcctgca gtgccagctc aagtgtaagt tacatgtact ggtaccagca gaagccagga    120
tcctccccca aaccctggat ttatcgcaca tccaacctgg cttctggagt ccctgctcgc    180
ttcagtggca gtgggtctgg gacctcttac tctctcacaa tcagcagcat ggaggctgaa    240
```
gatgctgcca cttattactg ccagcagtat catagttacc gggtcaacgt tcggtggggg    300
gaccaag                                                              307

<210> SEQ ID NO 20
<211> LENGTH: 307
<212> TYPE: DNA
<213> ORGANISM: Mus musculus

<400> SEQUENCE: 20
gatatcgttc tcacccaaac tacagcttct ttggctgtgt ctctagggca gagggccacc     60
atctcctgca gtgccagctc aagtgtaagt tacatgtact ggtaccagca gaagccagga    120
tcctccccca aaccctggat ttatcgcaca tccaacctgg cttctggagt ccctgctcgc    180
ttcagtggca gtgggtctgg gacctcttac tctctcacaa tcagcagcat ggaggctgaa    240
gatgctgcca cttattactg ccagcagtat catagttacc gggtcaacgt tcggtggggg    300
gaccaag                                                              307

<210> SEQ ID NO 21
<211> LENGTH: 284
<212> TYPE: DNA
<213> ORGANISM: Mus musculus

<400> SEQUENCE: 21
gatattgtta tgacccagac tccagcaatc atgtctgcat ctccagggga gaaggtcacc     60
atgacctgca gtgccagctc aagtgtaagt tacatgcact ggtaccagca gaagtcaggc    120
acctccccca aaagatggat ttatgacaca tccaaactgg cttctggagt ccctgctcgc    180
ttcagtggca gtgggtctgg gacctcttac tctctcacaa tcagcagcat ggaggctgaa    240
gatgctgcca cttattactg cctacattcg gagcgggcac cagg                     284

<210> SEQ ID NO 22
<211> LENGTH: 306
<212> TYPE: DNA
<213> ORGANISM: Mus musculus

<400> SEQUENCE: 22
gatgttgtta tgacacagac tacagcaatc atgtctgcat ctccagggga gaaggtcacc     60
atgacccgca gtgccagctc aagtgtaagt tacatgcact ggtaccagca gaagtcaggc    120
acctccccca aaagatggat ttatgacaca tccaaactgg cttctggagt ccctgctcgc    180
ttcagtggca gtgggtctgg gacttcttac cctctcacaa tcagcagcat ggaggctgaa    240
gatgctgcca cttattactg ccagcagtgg agtagtaacc caccgtacat cggcgcgggc    300
acaagg                                                               306

<210> SEQ ID NO 23
<211> LENGTH: 306
<212> TYPE: DNA
<213> ORGANISM: Mus musculus

<400> SEQUENCE: 23
gaagttgttc tcacacaaac tacagcaatc atgtctgcat ctccagggga gaaggtcacc     60
atgacctgca gtaccagctc aagtgtaagt tacatgcact ggtaccagca gaagtcaggc    120
acctccccca aaagatggat ttatgacaca tccaaactgg cttctggagt ccctgctcgc    180
ttcagtggca gtgggtctgg gacctcttac tctctcacaa tcagcagtgc ggaggctgaa    240
gatgctgcca cttattactg ccagcagtac agtggttgcc cactcacgtt cggcgagggc    300

| accaga | 306 |

<210> SEQ ID NO 24
<211> LENGTH: 305
<212> TYPE: DNA
<213> ORGANISM: Mus musculus

<400> SEQUENCE: 24

| gatatcgtta tcacacaaac tacagcaatc atgtctgcat ctccagggga gaaggtcacc | 60 |
| atatcctgca gtgccagctc aagtgtaagt tacatgtact ggtaccagca gaagccagga | 120 |
| tcctccccca aactctggat ttatagcaca tccaacctgg cttctggagt ccctgctcgc | 180 |
| ttcagtggca gtgggtctgg gacctcttac tctctcacaa tcagcagcat ggaggctgaa | 240 |
| gatgctgcca cttattactg ccagcagtat catagttacc ccctacattc ggcgctggga | 300 |
| caagg | 305 |

<210> SEQ ID NO 25
<211> LENGTH: 307
<212> TYPE: DNA
<213> ORGANISM: Mus musculus

<400> SEQUENCE: 25

| gtatattgtt atcacacagt ctccagcttc tttggctgtg tctctagggc agatggtcac | 60 |
| catgagctgc agggccagct caagtgtaaa ttacatgtac tggtaccagc agaagtcaga | 120 |
| tgcctccccc aaactatggt tttattacac atccaacctg gctcctggag tcccagctcg | 180 |
| cttcagtggc agtgggtctg ggaactctta ttctctcaca atcagcagca tggagggtga | 240 |
| agatgctgcc acttattact gccagcagtt tactagttcc ccggctgacg tcggcgctgg | 300 |
| cacaaag | 307 |

<210> SEQ ID NO 26
<211> LENGTH: 308
<212> TYPE: DNA
<213> ORGANISM: Mus musculus

<400> SEQUENCE: 26

| gtatattgtt atcacacagt ctccagcttc tttggctgtg tctctagggc agatggtcac | 60 |
| catgagctgc agggccagct caagtgtaaa ttacatgtac tggtaccagc agaagtcaga | 120 |
| tgcctccccc aaactatggt tttattacac atccaacctg gctcctggag tcccagctcg | 180 |
| cttcagtggc agtgggtctg ggaactctta ttctctcaca atcagcagca tggagggtga | 240 |
| agatgctgcc acttattact gcccgcagtt tactagttcc ccggctgacg ttcggcgctg | 300 |
| gcacaaag | 308 |

<210> SEQ ID NO 27
<211> LENGTH: 305
<212> TYPE: DNA
<213> ORGANISM: Mus musculus

<400> SEQUENCE: 27

| gatattgtgc tgacccagac tacagcaatc atgtctgcat ctctagggga gaaggtcacc | 60 |
| atgagctgca gggccagctc aagtgtaaat tacatgtact ggtaccagca gaagtcagat | 120 |
| gcctccccca aactatggat ttattacaca tccaacctgg ctcctggagt cccagctcgc | 180 |
| ttcagtggca gtgggtctgg gaactcttat tctctcacaa tcggcagcat ggagggtgaa | 240 |
| gatgctgcca cttattactg ccagcagttt actagttctc ccggacgttc ggtggggca | 300 |

```
caaag                                                          305

<210> SEQ ID NO 28
<211> LENGTH: 307
<212> TYPE: DNA
<213> ORGANISM: Mus musculus

<400> SEQUENCE: 28
gatattgtga tcacacaaac tacagcaatc atgtctgcat ctctagggga gaaggtcacc    60
atgagctgca gggccagctc aagtgtaaat tacatgtact ggtaccagca gaagtcagat   120
gcctccccca aactatggat ttattacaca tccaacctgg ctcctggagt cccagctcgc   180
ttcagtggca gtgggtctgg gaactcttat tctctcacaa tcagcagcat ggagggtgaa   240
gatgctgcca cttattactg ccagcagttt actagttccc ttacacacat tcggagcagg   300
cacaagg                                                            307

<210> SEQ ID NO 29
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 29

Gly Glu Ala Gly Ala Glu Leu Val Lys Pro Gly Ala Ser Val Lys Leu
 1               5                  10                  15

Ser Cys Thr Ala Ser
            20

<210> SEQ ID NO 30
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 30

Gly Phe Asn Ile Lys Asp Thr Tyr Met His
 1               5                  10

<210> SEQ ID NO 31
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 31

Trp Val Lys Gln Arg Pro Glu Gln Gly Leu Glu Trp Ile Gly
 1               5                  10

<210> SEQ ID NO 32
<211> LENGTH: 22
<212> TYPE: PRT
<213> ORGANISM: Artificial Sequence
<220> FEATURE:
<223> OTHER INFORMATION: Synthetically generated peptide

<400> SEQUENCE: 32

Gly Ala Ala Ala Gly Ala Glu Leu Val Lys Pro Gly Ala Ser Val Lys
 1               5                  10                  15

Leu Ser Cys Thr Ala Ser
```

<210> SEQ ID NO 33
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 33

Gly Phe Asn Ile Lys Asp Thr Tyr Met His
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 34

Trp Val Lys Gln Arg Pro Glu Gln Gly Leu Glu Trp Ile Gly
1               5                   10

<210> SEQ ID NO 35
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 35

Gly Ala Ala Gly Pro Glu Leu Val Arg Ser Gly Ala Ser Val Lys Leu
1               5                   10                  15

Ser Cys Thr Ala Ser
            20

<210> SEQ ID NO 36
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 36

Gly Phe Asn Ile Lys Asp Tyr Tyr Met His
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 37

Trp Val Lys Gln Arg Pro Glu Gln Gly Leu Glu Trp Ile Gly
1               5                   10

<210> SEQ ID NO 38
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 38

```
Gly Ala Ala Gly Ala Glu Leu Val Arg Ser Gly Ala Ser Val Lys Leu
1               5                   10                  15

Ser Cys Thr Ala Ser
            20
```

<210> SEQ ID NO 39
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 39

```
Gly Phe Asn Ile Lys Asp Tyr Tyr Met His
1               5                   10
```

<210> SEQ ID NO 40
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 40

```
Trp Val Lys Gln Arg Pro Glu Gln Gly Leu Glu Trp Ile Gly
1               5                   10
```

<210> SEQ ID NO 41
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 41

```
Gln Val Leu Leu Leu Glu Ser Gly Gly Gly Leu Val Gln Pro Gly Gly
1               5                   10                  15

Ser Met Lys Leu Ser Cys Ala Ala Ser
            20                  25
```

<210> SEQ ID NO 42
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 42

```
Gly Phe Thr Phe Ser Asp Ala Trp Met Asp
1               5                   10
```

<210> SEQ ID NO 43
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 43

```
Trp Val Arg Gln Ser Pro Glu Lys Gly Leu Glu Trp Val Ala
1               5                   10
```

<210> SEQ ID NO 44
<211> LENGTH: 22
<212> TYPE: PRT

```
<213> ORGANISM: Artificial Sequence
<220> FEATURE:
<223> OTHER INFORMATION: Synthetically generated peptide

<400> SEQUENCE: 44

Ser Asp Ala Ala Gly Gly Gly Leu Val Gln Pro Gly Gly Ser Met Lys
 1               5                  10                  15

Leu Ser Cys Val Ala Ser
            20

<210> SEQ ID NO 45
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 45

Gly Phe Thr Phe Ser Asn Tyr Trp Met Asn
 1               5                  10

<210> SEQ ID NO 46
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 46

Trp Val Arg Gln Ser Pro Glu Lys Gly Leu Glu Trp Val Ala
 1               5                  10

<210> SEQ ID NO 47
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 47

Gly Asp Ala Ala Ala Gly Leu Val Gln Pro Gly Gly Ser Met Lys Leu
 1               5                  10                  15

Ser Cys Val Ala Ser
            20

<210> SEQ ID NO 48
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 48

Gly Phe Thr Phe Ser Asn Tyr Trp Met Asn
 1               5                  10

<210> SEQ ID NO 49
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 49

Trp Val Arg Gln Ser Pro Glu Lys Gly Leu Glu Trp Val Ala
 1               5                  10
```

<210> SEQ ID NO 50
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 50

Gly Ala Ala Gly Gly Gly Leu Val Gln Pro Gly Gly Ser Met Lys Leu
1               5                   10                  15

Ser Cys Val Ala Ser
            20

<210> SEQ ID NO 51
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 51

Gly Phe Thr Phe Ser Asn Tyr Trp Met Asn
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 52

Trp Val Arg Gln Ser Pro Glu Lys Gly Leu Glu Trp Val Ala
1               5                   10

<210> SEQ ID NO 53
<211> LENGTH: 22
<212> TYPE: PRT
<213> ORGANISM: Artificial Sequence
<220> FEATURE:
<223> OTHER INFORMATION: Synthetically generated peptide

<400> SEQUENCE: 53

Gly Asp Ala Gly Gly Gly Gly Leu Val Gln Pro Gly Gly Ser Met Lys
1               5                   10                  15

Leu Ser Cys Val Ala Ser
            20

<210> SEQ ID NO 54
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 54

Gly Phe Thr Phe Ser Asn Tyr Trp Met Asn
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Synthetically generated peptide

```
<400> SEQUENCE: 55

Trp Val Arg Gln Ser Pro Glu Lys Gly Leu Glu Trp Val Ala
1               5                   10

<210> SEQ ID NO 56
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 56

Gly Ala Ala Gly Gly Leu Val Gln Pro Gly Gly Ser Met Lys Leu Ser
1               5                   10                  15

Cys Val Ala Ser
            20

<210> SEQ ID NO 57
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 57

Gly Phe Thr Phe Ser Asn Tyr Trp Met Asn
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 58

Trp Val Arg Gln Ser Pro Glu Lys Gly Leu Glu Trp Val Ala
1               5                   10

<210> SEQ ID NO 59
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 59

Gly Ala Ala Gly Gly Leu Val Gln Pro Gly Gly Pro Met Lys Leu Ser
1               5                   10                  15

Cys Val Ala Ser
            20

<210> SEQ ID NO 60
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 60

Gly Phe Thr Phe Ser Asn Tyr Trp Met Ser
1               5                   10

<210> SEQ ID NO 61
```

```
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 61

Trp Val Arg Gln Ser Pro Glu Lys Gly Leu Glu Trp Val Ala
1               5                   10

<210> SEQ ID NO 62
<211> LENGTH: 24
<212> TYPE: PRT
<213> ORGANISM: Artificial Sequence
<220> FEATURE:
<223> OTHER INFORMATION: Synthetically generated peptide

<400> SEQUENCE: 62

Val Lys Leu Glu Gln Ser Gly Pro Glu Leu Val Lys Pro Gly Ala Ser
1               5                   10                  15

Val Lys Ile Ser Cys Lys Ala Ser
            20

<210> SEQ ID NO 63
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 63

Gly Tyr Ser Phe Thr Gly Tyr Phe Met Asn
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 64

Trp Val Met Gln Ser His Gly Lys Ser Leu Glu Trp Ile Gly
1               5                   10

<210> SEQ ID NO 65
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 65

Glu Ile Val Met Thr Gln Thr Pro Ala Ser Leu Ser Met Ala Ile Gly
1               5                   10                  15

Glu Lys Val Thr Ile Arg Cys
            20

<210> SEQ ID NO 66
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 66
```

Ile Thr Ser Thr Asp Ile Asp Asp Met Asn
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 67

Trp Tyr Gln Gln Lys Pro Gly Glu Pro Pro Asn Leu Leu
1               5                   10

<210> SEQ ID NO 68
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 68

Lys Ser Val Met Thr Gln Thr Pro Leu Thr Leu Ser Val Thr Ile Gly
1               5                   10                  15

Gln Pro Ala Ser Ile Ser Cys
            20

<210> SEQ ID NO 69
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 69

Lys Ser Ser Gln Ser Leu Leu Asp Ser Asp Gly Lys Thr Tyr Leu Asn
1               5                   10                  15

<210> SEQ ID NO 70
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 70

Trp Leu Leu Gln Arg Pro Gly Gln Ser Pro Lys Arg Leu
1               5                   10

<210> SEQ ID NO 71
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 71

Asp Val Val Leu Thr Gln Thr Pro Leu Thr Leu Ser Val Thr Ile Gly
1               5                   10                  15

Gln Pro Ala Ser Ile Ser Cys
            20

<210> SEQ ID NO 72
<211> LENGTH: 16
<212> TYPE: PRT
<213> ORGANISM: Artificial Sequence

```
<220> FEATURE:
<223> OTHER INFORMATION: Synthetically generated peptide

<400> SEQUENCE: 72

Lys Ser Ser Gln Ser Leu Leu Asp Ser Asp Gly Lys Thr Tyr Leu Asn
1               5                   10                  15

<210> SEQ ID NO 73
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 73

Trp Leu Leu Gln Arg Pro Gly Gln Ser Pro Lys Arg Leu
1               5                   10

<210> SEQ ID NO 74
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 74

Asp Val Val Leu Thr Gln Thr Pro Ala Ser Leu Ala Val Ser Leu Gly
1               5                   10                  15

Gln Arg Ala Thr Ile Ser Cys
            20

<210> SEQ ID NO 75
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 75

Arg Ala Ser Glu Ser Val Asp Asn Tyr Gly Ile Ser Phe Met Asn
1               5                   10                  15

<210> SEQ ID NO 76
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 76

Trp Phe Gln Gln Lys Pro Gly Gln Pro Pro Lys Leu Leu
1               5                   10

<210> SEQ ID NO 77
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 77

Asp Val Val Ile Thr Gln Thr Thr Ala Ser Leu Ala Val Ser Leu Gly
1               5                   10                  15

Gln Arg Ala Thr Ile Ser Cys
            20
```

<210> SEQ ID NO 78
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 78

Arg Ala Ser Glu Ser Val Asp Asn Tyr Gly Ile Ser Phe Met Asn
 1               5                  10                  15

<210> SEQ ID NO 79
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 79

Trp Phe Pro Thr Glu Thr Arg Thr Ala Thr Gln Thr Pro His Leu Cys
 1               5                  10                  15

Cys

<210> SEQ ID NO 80
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 80

Glu Ile Val Ile Thr Gln Ser Pro Ala Ser Leu Ala Val Ser Leu Gly
 1               5                  10                  15

Gln Arg Ala Thr Ile Phe Cys
            20

<210> SEQ ID NO 81
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 81

Arg Ala Ser Gln Ser Val Asp Tyr Asn Gly Ile Ser Tyr Met His
 1               5                  10                  15

<210> SEQ ID NO 82
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 82

Trp Phe Gln Gln Lys Pro Gly Gln Pro Pro Lys Leu Leu
 1               5                  10

<210> SEQ ID NO 83
<211> LENGTH: 22
<212> TYPE: PRT
<213> ORGANISM: Artificial Sequence
<220> FEATURE:
<223> OTHER INFORMATION: Synthetically generated peptide

<400> SEQUENCE: 83

```
Val Val Met Thr Gln Ser Pro Ala Ile Met Ser Ala Ser Leu Gly Glu
1               5                   10                  15

Arg Val Thr Met Thr Cys
            20
```

<210> SEQ ID NO 84
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 84

```
Thr Ala Ser Ser Ser Val Ser Ser Ser Tyr Leu His
1               5                   10
```

<210> SEQ ID NO 85
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 85

```
Trp Tyr Gln Gln Lys Pro Gly Ser Ser Pro Lys Leu Trp
1               5                   10
```

<210> SEQ ID NO 86
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 86

```
Asp Ile Val Leu Thr Gln Thr Thr Ala Ile Met Ser Ala Ser Leu Gly
1               5                   10                  15

Glu Arg Val Thr Met Thr Cys
            20
```

<210> SEQ ID NO 87
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 87

```
Thr Ala Ser Ser Ser Val Ser Ser Ser Tyr Leu His
1               5                   10
```

<210> SEQ ID NO 88
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 88

```
Trp Tyr Gln Gln Lys Pro Gly Ser Ser Pro Lys Leu Trp
1               5                   10
```

<210> SEQ ID NO 89
<211> LENGTH: 22
<212> TYPE: PRT

<213> ORGANISM: Artificial Sequence
<220> FEATURE:
<223> OTHER INFORMATION: Synthetically generated peptide

<400> SEQUENCE: 89

Ile Val Leu Thr Gln Thr Thr Ala Ile Met Ser Ala Ser Leu Gly Glu
1               5                   10                  15

Arg Val Thr Met Thr Cys
            20

<210> SEQ ID NO 90
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 90

Thr Ala Ser Ser Ser Val Ser Ser Ser Tyr Leu His
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 91

Trp Tyr Gln Gln Lys Pro Gly Ser Ser Pro Lys Leu Trp
1               5                   10

<210> SEQ ID NO 92
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 92

Asp Val Val Met Thr Gln Thr Thr Ala Ile Met Ser Ala Ser Leu Gly
1               5                   10                  15

Glu Arg Val Thr Met Thr Cys
            20

<210> SEQ ID NO 93
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 93

Thr Ala Ser Ser Ser Val Ser Ser Ser Tyr Leu His
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 94

Trp Tyr Gln Gln Lys Pro Gly Ser Ser Pro Lys Leu Trp
1               5                   10

<210> SEQ ID NO 95
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 95

Asp Val Val Leu Thr Gln Thr Thr Ala Ile Met Ser Ala Ser Leu Gly
1               5                   10                  15
Glu Arg Val Thr Met Thr Cys
            20

<210> SEQ ID NO 96
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 96

Thr Ala Ser Ser Ser Val Ser Ser Ser Tyr Leu His
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 97

Trp Tyr Gln Gln Lys Pro Gly Ser Ser Pro Lys Leu Trp
1               5                   10

<210> SEQ ID NO 98
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 98

Glu Val Val Ile Thr Gln Thr Pro Ala Ile Met Ser Ala Ser Leu Gly
1               5                   10                  15
Glu Arg Val Thr Met Thr Cys
            20

<210> SEQ ID NO 99
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 99

Thr Ala Ser Ser Ser Val Ser Ser Ser Tyr Leu His
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Synthetically generated peptide

```
<400> SEQUENCE: 100

Trp Tyr Gln Gln Lys Pro Gly Ser Ser Pro Lys Leu Trp
 1               5                  10

<210> SEQ ID NO 101
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 101

Asp Val Val Leu Thr Gln Thr Thr Ala Ile Met Ser Ala Ser Leu Gly
 1               5                  10                  15

Glu Arg Val Thr Met Thr Cys
            20

<210> SEQ ID NO 102
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 102

Thr Ala Ser Ser Ser Val Ser Ser Ser Tyr Leu His
 1               5                  10

<210> SEQ ID NO 103
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 103

Trp Tyr Gln Gln Lys Pro Gly Ser Ser Pro Lys Leu Trp
 1               5                  10

<210> SEQ ID NO 104
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 104

Glu Ile Val Met Thr Gln Ser Thr Ala Ile Met Ser Ala Ser Leu Gly
 1               5                  10                  15

Glu Arg Val Thr Met Thr Cys
            20

<210> SEQ ID NO 105
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 105

Thr Ala Ser Ser Ser Val Ser Ser Ser Tyr Leu His
 1               5                  10

<210> SEQ ID NO 106
```

```
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 106

Trp Tyr Gln Gln Lys Pro Gly Ser Ser Pro Lys Leu Trp
 1               5                  10

<210> SEQ ID NO 107
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 107

Arg Ile Asp Pro Ala Asn Gly Asn Thr Lys Tyr Asp Pro Lys Phe Gln
 1               5                  10                  15

Gly

<210> SEQ ID NO 108
<211> LENGTH: 32
<212> TYPE: PRT
<213> ORGANISM: Artificial Sequence
<220> FEATURE:
<223> OTHER INFORMATION: Synthetically generated peptide

<400> SEQUENCE: 108

Lys Ala Thr Ile Thr Ala Asp Thr Ser Ser Asn Thr Ala Tyr Leu Gln
 1               5                  10                  15

Leu Ser Ser Leu Thr Ser Gly Asp Thr Ala Val Tyr Tyr Cys Ala Ser
            20                  25                  30

<210> SEQ ID NO 109
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 109

Arg Ile Asp Pro Ala Asn Gly Asn Thr Lys Tyr Asp Pro Lys Phe Gln
 1               5                  10                  15

Gly

<210> SEQ ID NO 110
<211> LENGTH: 32
<212> TYPE: PRT
<213> ORGANISM: Artificial Sequence
<220> FEATURE:
<223> OTHER INFORMATION: Synthetically generated peptide

<400> SEQUENCE: 110

Lys Ala Thr Ile Thr Ala Asp Thr Ser Ser Asn Thr Ala Tyr Leu Gln
 1               5                  10                  15

Leu Ser Ser Leu Thr Ser Glu Asp Thr Ala Val Tyr Tyr Cys Ala Arg
            20                  25                  30

<210> SEQ ID NO 111
<211> LENGTH: 17
<212> TYPE: PRT
<213> ORGANISM: Artificial Sequence
<220> FEATURE:
```

<223> OTHER INFORMATION: Synthetically generated peptide

<400> SEQUENCE: 111

Trp Ile Asp Pro Glu Asn Gly Asp Thr Glu Tyr Ala Pro Lys Phe Gln
1               5                   10                  15
Gly

<210> SEQ ID NO 112
<211> LENGTH: 32
<212> TYPE: PRT
<213> ORGANISM: Artificial Sequence
<220> FEATURE:
<223> OTHER INFORMATION: Synthetically generated peptide

<400> SEQUENCE: 112

Lys Ala Thr Met Thr Ala Asp Thr Ser Ser Asn Thr Ala Tyr Leu Gln
1               5                   10                  15
Leu Ser Ser Leu Thr Ser Glu Asp Thr Ala Val Tyr Tyr Cys Ser Gly
            20                  25                  30

<210> SEQ ID NO 113
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 113

Trp Ile Asp Pro Glu Asn Gly Asp Thr Glu Tyr Ala Pro Lys Phe Gln
1               5                   10                  15
Gly

<210> SEQ ID NO 114
<211> LENGTH: 32
<212> TYPE: PRT
<213> ORGANISM: Artificial Sequence
<220> FEATURE:
<223> OTHER INFORMATION: Synthetically generated peptide

<400> SEQUENCE: 114

Lys Ala Thr Met Thr Ala Asp Thr Ser Ser Asn Thr Ala Tyr Leu Gln
1               5                   10                  15
Leu Ser Ser Leu Thr Ser Glu Asp Thr Ala Val Tyr Tyr Cys Asn Ala
            20                  25                  30

<210> SEQ ID NO 115
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 115

Glu Ile Arg Ser Lys Ala Asn Asn His Ala Thr Tyr Tyr Ala Glu Ser
1               5                   10                  15
Val Lys Gly

<210> SEQ ID NO 116
<211> LENGTH: 32
<212> TYPE: PRT
<213> ORGANISM: Artificial Sequence
<220> FEATURE:
<223> OTHER INFORMATION: Synthetically generated peptide -continued

```
<400> SEQUENCE: 116

Arg Phe Thr Ile Ser Arg Asp Asp Ser Lys Ser Ser Val Tyr Leu Gln
1               5                   10                  15

Met Asn Ser Leu Arg Ala Glu Asp Thr Gly Ile Tyr Tyr Cys Thr Arg
            20                  25                  30

<210> SEQ ID NO 117
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 117

Glu Ile Arg Leu Lys Pro Asn Asn Tyr Ala Thr His Tyr Ala Glu Ser
1               5                   10                  15

Val Lys Gly

<210> SEQ ID NO 118
<211> LENGTH: 32
<212> TYPE: PRT
<213> ORGANISM: Artificial Sequence
<220> FEATURE:
<223> OTHER INFORMATION: Synthetically generated peptide

<400> SEQUENCE: 118

Arg Phe Thr Ile Ser Arg Asp Asp Ser Lys Ser Ser Val Tyr Leu Gln
1               5                   10                  15

Met Asn Asn Leu Arg Ala Glu Asp Thr Gly Ile Tyr Tyr Cys Thr Arg
            20                  25                  30

<210> SEQ ID NO 119
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 119

Glu Ile Arg Leu Lys Ser Asn Asn Tyr Ala Ile His Tyr Ala Glu Ser
1               5                   10                  15

Val Lys Gly

<210> SEQ ID NO 120
<211> LENGTH: 32
<212> TYPE: PRT
<213> ORGANISM: Artificial Sequence
<220> FEATURE:
<223> OTHER INFORMATION: Synthetically generated peptide

<400> SEQUENCE: 120

Arg Phe Thr Ile Ser Arg Asp Asp Ser Lys Ser Ser Val Tyr Leu Gln
1               5                   10                  15

Met Asn Asn Leu Arg Ala Glu Asp Thr Gly Ile Tyr Tyr Cys Thr Arg
            20                  25                  30

<210> SEQ ID NO 121
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 121
```

Glu Ile Arg Leu Lys Ser Asn Asn Tyr Ala Thr His Tyr Ala Glu Ser
1               5                   10                  15

Val Lys Gly

<210> SEQ ID NO 122
<211> LENGTH: 33
<212> TYPE: PRT
<213> ORGANISM: Artificial Sequence
<220> FEATURE:
<223> OTHER INFORMATION: Synthetically generated peptide

<400> SEQUENCE: 122

Arg Phe Thr Ile Ser Arg Asp Asp Ser Lys Ser Ser Val Tyr Leu Gln
1               5                   10                  15

Met Asn Asn Leu Arg His Val Gly Pro Arg Asn Leu Cys His Cys Leu
                20                  25                  30

Leu

<210> SEQ ID NO 123
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 123

Glu Ile Arg Leu Lys Ser Asn Asn Tyr Ala Thr His Tyr Ala Glu Ser
1               5                   10                  15

Val Lys Gly

<210> SEQ ID NO 124
<211> LENGTH: 32
<212> TYPE: PRT
<213> ORGANISM: Artificial Sequence
<220> FEATURE:
<223> OTHER INFORMATION: Synthetically generated peptide

<400> SEQUENCE: 124

Arg Phe Thr Ile Ser Arg Asp Asp Ser Lys Ser Ser Val Tyr Leu Gln
1               5                   10                  15

Met Asn Asn Leu Arg Ala Glu Asp Thr Gly Ile Tyr Tyr Cys Thr Arg
                20                  25                  30

<210> SEQ ID NO 125
<211> LENGTH: 19
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = any amino acid

<400> SEQUENCE: 125

Glu Xaa Arg Leu Lys Ser Asn Asn Tyr Ala Thr His Tyr Ala Glu Ser
1               5                   10                  15

Val Lys Gly

<210> SEQ ID NO 126
<211> LENGTH: 32
<212> TYPE: PRT
<213> ORGANISM: Artificial Sequence

```
<220> FEATURE:
<223> OTHER INFORMATION: Synthetically generated peptide

<400> SEQUENCE: 126

Arg Phe Thr Ile Ser Arg Asp Asp Ser Lys Ser Ser Val Tyr Leu Gln
 1               5                  10                  15

Met Asn Asn Leu Arg Ala Glu Asp Thr Gly Ile Tyr Tyr Cys Thr Arg
                20                  25                  30

<210> SEQ ID NO 127
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 127

Glu Ile Arg Leu Lys Ser Asn Asn Tyr Ala Thr His Tyr Ala Glu Ser
 1               5                  10                  15

Val Lys Gly

<210> SEQ ID NO 128
<211> LENGTH: 32
<212> TYPE: PRT
<213> ORGANISM: Artificial Sequence
<220> FEATURE:
<223> OTHER INFORMATION: Synthetically generated peptide

<400> SEQUENCE: 128

Arg Phe Thr Ile Ser Gly Asp Asp Ser Lys Ser Ser Val Tyr Leu Gln
 1               5                  10                  15

Met Asn Ser Leu Arg Ala Glu Asp Thr Gly Ile Tyr Tyr Cys Thr Arg
                20                  25                  30

<210> SEQ ID NO 129
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 129

Arg Ile Asn Pro Tyr Asn Gly Asp Thr Phe Tyr Asn Gln Lys Phe Lys
 1               5                  10                  15

Gly

<210> SEQ ID NO 130
<211> LENGTH: 32
<212> TYPE: PRT
<213> ORGANISM: Artificial Sequence
<220> FEATURE:
<223> OTHER INFORMATION: Synthetically generated peptide

<400> SEQUENCE: 130

Lys Ala Thr Leu Thr Val Asp Lys Ser Ser Ser Thr Ala His Met Glu
 1               5                  10                  15

Leu Arg Ser Leu Ala Ser Glu Asp Ser Ala Val Tyr Tyr Cys Ala Arg
                20                  25                  30

<210> SEQ ID NO 131
<211> LENGTH: 3
<212> TYPE: PRT
<213> ORGANISM: Artificial Sequence
<220> FEATURE:
```

<223> OTHER INFORMATION: Synthetically generated peptide

<400> SEQUENCE: 131

Ile Ser Glu
 1

<210> SEQ ID NO 132
<211> LENGTH: 38
<212> TYPE: PRT
<213> ORGANISM: Artificial Sequence
<220> FEATURE:
<223> OTHER INFORMATION: Synthetically generated peptide

<400> SEQUENCE: 132

Asp Asn Thr Leu Arg Pro Gly Val Pro Ser Arg Phe Ser Ser Gly
 1               5                  10                  15

Tyr Gly Thr Asp Phe Val Phe Thr Ile Glu Asn Met Leu Ser Glu Asp
                20                  25                  30

Ala Ala Asp Tyr Tyr Cys
            35

<210> SEQ ID NO 133
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 133

Ile Tyr Leu Val Ser Lys Leu
 1               5

<210> SEQ ID NO 134
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 134

Asp Ser Gly Val Pro Asp Arg Phe Thr Gly Ser Gly Ser Gly Thr Asp
 1               5                  10                  15

Phe Thr Leu Lys Ile Ser Arg Val Glu Ala Glu Asp Leu Gly Val Tyr
                20                  25                  30

Tyr Cys

<210> SEQ ID NO 135
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 135

Ile Tyr Gln Val Ser Lys Leu
 1               5

<210> SEQ ID NO 136
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 136

```
Asp Ser Gly Val Pro Asp Arg Phe Thr Gly Ser Gly Ser Gly Thr Asp
 1               5                  10                  15

Phe Thr Leu Lys Ile Ser Arg Val Glu Ala Glu Asp Leu Gly Val Tyr
                 20                  25                  30

Tyr Cys
```

<210> SEQ ID NO 137
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 137

```
Ile Tyr Ala Asn Gln
 1               5
```

<210> SEQ ID NO 138
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 138

```
Gly Ser Gly Val Pro Ala Arg Phe Ser Gly Ser Gly Ser Gly Thr Asp
 1               5                  10                  15

Phe Ser Leu Asn Ile His Pro Met Glu Lys Asp Asp Thr Ala Met Tyr
                 20                  25                  30

Phe Cys
```

<210> SEQ ID NO 139
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 139

```
Leu Gln Pro Arg Ile Arg Gly
 1               5
```

<210> SEQ ID NO 140
<211> LENGTH: 32
<212> TYPE: PRT
<213> ORGANISM: Artificial Sequence
<220> FEATURE:
<223> OTHER INFORMATION: Synthetically generated peptide

<400> SEQUENCE: 140

```
Pro Cys His Val Trp Gln Trp Val Trp Asp Arg Leu Ser Leu Asn Ile
 1               5                  10                  15

His Pro Met Glu Glu Asp Asp Thr Ala Met Tyr Phe Cys Gln Gln Ser
                 20                  25                  30
```

<210> SEQ ID NO 141
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 141

```
Ile Tyr Ala Asn Leu
1               5
```

<210> SEQ ID NO 142
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 142

```
Glu Ser Gly Ile Pro Ala Arg Phe Ser Gly Ser Gly Ser Gly Thr Asp
1               5                   10                  15

Phe Thr Leu Asn Ile His Pro Val Glu Glu Asp Ala Ala Thr Tyr
            20                  25                  30

Tyr Cys
```

<210> SEQ ID NO 143
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 143

```
Ile Tyr Ser Thr Ser Asn Leu
1               5
```

<210> SEQ ID NO 144
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 144

```
Ala Ser Gly Val Pro Ala Arg Phe Ser Gly Ser Gly Ser Gly Thr Ser
1               5                   10                  15

Tyr Ser Leu Thr Ile Ser Ser Met Glu Ala Glu Asp Ala Ala Thr Tyr
            20                  25                  30

Tyr Cys
```

<210> SEQ ID NO 145
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 145

```
Ile Tyr Ser Thr Ser Asn Leu
1               5
```

<210> SEQ ID NO 146
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 146

```
Ala Ser Gly Val Pro Ala Arg Phe Ser Gly Ser Gly Ser Gly Thr Ser
1               5                   10                  15

Tyr Ser Leu Thr Ile Ser Ser Met Glu Ala Glu Asp Ala Ala Thr Tyr
```

```
              20                  25                  30

Tyr Cys

<210> SEQ ID NO 147
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 147

Ile Tyr Ser Thr Ser Asn Leu
1               5

<210> SEQ ID NO 148
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 148

Ala Ser Gly Val Pro Ala Arg Phe Ser Gly Ser Gly Ser Gly Thr Ser
1               5                   10                  15

Tyr Ser Leu Thr Ile Ser Ser Met Glu Ala Glu Asp Ala Ala Thr Tyr
            20                  25                  30

Tyr Cys

<210> SEQ ID NO 149
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 149

Ile Tyr Ser Thr Ser Asn Leu
1               5

<210> SEQ ID NO 150
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 150

Ala Ser Gly Val Pro Ala Arg Phe Ser Gly Ser Gly Ser Gly Thr Ser
1               5                   10                  15

Tyr Ser Leu Thr Ile Ser Ser Met Glu Ala Glu Asp Ala Ala Thr Tyr
            20                  25                  30

Tyr Cys

<210> SEQ ID NO 151
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 151

Ile Tyr Ser Thr Ser Asn Leu
1               5
```

<210> SEQ ID NO 152
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 152

Ala Ser Gly Val Pro Ala Arg Phe Ser Gly Ser Gly Ser Gly Thr Ser
1               5                   10                  15

Tyr Ser Phe Thr Ile Ser Ser Met Glu Ala Glu Asp Ala Ala Thr Tyr
            20                  25                  30

Tyr Cys

<210> SEQ ID NO 153
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 153

Ile Tyr Ser Thr Ser Asn Leu
1               5

<210> SEQ ID NO 154
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 154

Ala Ser Gly Val Pro Ala Arg Phe Ser Gly Ser Gly Ser Gly Thr Ser
1               5                   10                  15

Tyr Ser Leu Thr Ile Ser Ser Met Glu Ala Glu Asp Ala Ala Thr Tyr
            20                  25                  30

Tyr Cys

<210> SEQ ID NO 155
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 155

Ile Tyr Ser Thr Ser Asn Leu
1               5

<210> SEQ ID NO 156
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 156

Ala Ser Gly Val Pro Ala Arg Phe Ser Gly Ser Gly Ser Gly Thr Ser
1               5                   10                  15

Tyr Ser Leu Thr Ile Ser Ser Met Glu Ala Glu Asp Ala Ala Ala Tyr
            20                  25                  30

Tyr Cys

```
<210> SEQ ID NO 157
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 157

Ile Tyr Ser Thr Tyr Asn Leu
1               5

<210> SEQ ID NO 158
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 158

Ala Ser Gly Val Pro Ala Arg Phe Ser Gly Ser Gly Ser Gly Thr Ser
1               5                   10                  15

His Ser Leu Thr Ile Ser Ser Met Glu Ala Glu Asp Ala Ala Thr Tyr
            20                  25                  30

Tyr Cys

<210> SEQ ID NO 159
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 159

Asn Arg Asp Trp Phe Ala Leu
1               5

<210> SEQ ID NO 160
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 160

Trp Gly Pro Gly Thr Leu Leu Thr Val Ser Ser
1               5                   10

<210> SEQ ID NO 161
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 161

Thr Asp Tyr Pro Phe Tyr Ala Met Val Val Gly Trp Arg Asn Tyr Thr
1               5                   10                  15

Leu Leu

<210> SEQ ID NO 162
<211> LENGTH: 10
<212> TYPE: PRT
<213> ORGANISM: Artificial Sequence
<220> FEATURE:
```

<223> OTHER INFORMATION: Synthetically generated peptide

<400> SEQUENCE: 162

Gly Ala Lys Glu Pro Leu Ser Leu Ser Leu
1               5                   10

<210> SEQ ID NO 163
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 163

Pro Phe Tyr Asp Gly Pro Leu Val Cys Trp Leu Gly Ser Arg Asn Ser
1               5                   10                  15

Ala His Cys Leu Leu
            20

<210> SEQ ID NO 164
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 164

His Pro Gly His Arg Leu Arg
1               5

<210> SEQ ID NO 165
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 165

Pro Gly Tyr Arg Tyr Asp Arg His Thr Gly Ala Gln Ala Pro Arg Ser
1               5                   10                  15

Leu Ser Pro

<210> SEQ ID NO 166
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 166

Arg Asn Trp Tyr Phe Gly Val
1               5

<210> SEQ ID NO 167
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 167

Trp Gly Gln Gly Thr Pro Leu Thr Val Ser Ala
1               5                   10

<210> SEQ ID NO 168

```
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 168

Asn Tyr Thr His Cys Leu Arg
1               5

<210> SEQ ID NO 169
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 169

Arg Asn Trp Tyr Phe Asp Tyr
1               5

<210> SEQ ID NO 170
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 170

Trp Gly Glu Gly His Pro Ser His Cys Leu Leu
1               5                   10

<210> SEQ ID NO 171
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 171

Asp Tyr Gly Tyr Asp Gly Asp
1               5

<210> SEQ ID NO 172
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 172

Trp Gly Ala Gly Thr Ser Leu Thr Val Ser Ala
1               5                   10

<210> SEQ ID NO 173
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 173

Val Gly Val Arg Asn Tyr Phe Asp Ile Trp Gly Pro Gly Thr Ser Val
1               5                   10                  15

Thr Val Ser Ala
            20
```

```
<210> SEQ ID NO 174
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 174

Leu Gln Ser Asp Asn Leu Pro Leu Asp Val Arg Arg Arg Glu Ser Trp
 1               5                  10                  15

Arg

<210> SEQ ID NO 175
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 175

Trp Gln Gly Thr His Phe Pro Val Thr
 1               5

<210> SEQ ID NO 176
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 176

Phe Gly Ala Gly Thr Arg Leu Glu Ile
 1               5

<210> SEQ ID NO 177
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 177

Trp Gln Gly Thr Leu Arg Ser Val Val Ala Gln Asn Trp Arg
 1               5                  10

<210> SEQ ID NO 178
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 178

Gln Gln Val Arg Arg Phe Pro Asp Thr Phe Gly Ala Gly Thr Arg Leu
 1               5                  10                  15

Glu Ile

<210> SEQ ID NO 179
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 179
```

```
Lys Glu Val Pro Val Asn Ile Arg Arg Arg His Lys Ala Gly Asp
  1               5                  10                  15
```

<210> SEQ ID NO 180
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 180

```
Gln Gln Ser Ile Glu Asp Pro Tyr Thr
  1               5
```

<210> SEQ ID NO 181
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 181

```
Phe Gly Gly Gly Thr Lys Leu Glu Ile
  1               5
```

<210> SEQ ID NO 182
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 182

```
His Gln Tyr His Arg Ser Leu Gly Thr
  1               5
```

<210> SEQ ID NO 183
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 183

```
Phe Gly Ala Gly Thr Lys Leu Glu Ile
  1               5
```

<210> SEQ ID NO 184
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 184

```
His Gln Tyr His Arg Ser Pro Asp Thr
  1               5
```

<210> SEQ ID NO 185
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 185

```
Phe Gly Ala Gly Thr Arg Leu Glu Ile
```

```
<210> SEQ ID NO 186
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 186

His Gln Tyr His Arg Ser Pro Gly His Val Arg Arg Arg Asp Lys Thr
1               5                   10                  15

Gly Asn

<210> SEQ ID NO 187
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 187

His Gln Tyr His Arg Ser Pro Pro Asp Ile Arg Arg Arg His Lys Thr
1               5                   10                  15

Gly Asn

<210> SEQ ID NO 188
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 188

His Gln Tyr His Arg Ser Pro Arg Asn Ile Arg Arg Arg His Gln Thr
1               5                   10                  15

Gly Asn

<210> SEQ ID NO 189
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 189

His Gln Tyr His Arg Ser Thr His Val Arg Trp Gly His Lys Ala Gly
1               5                   10                  15

Asp

<210> SEQ ID NO 190
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 190

Gln Gln Tyr His Ser Tyr Pro Pro Asp Thr
1               5                   10

<210> SEQ ID NO 191
<211> LENGTH: 9
<212> TYPE: PRT
```

```
<213> ORGANISM: Artificial Sequence
<220> FEATURE:
<223> OTHER INFORMATION: Synthetically generated peptide

<400> SEQUENCE: 191

Phe Gly Gly Gly Thr Lys Leu Glu Ile
 1               5

<210> SEQ ID NO 192
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 192

His Gln Tyr His Arg Ser Pro Phe Thr
 1               5

<210> SEQ ID NO 193
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 193

Phe Gly Glu Gly Thr Arg Leu Glu Ile
 1               5

<210> SEQ ID NO 194
<211> LENGTH: 15
<212> TYPE: DNA
<213> ORGANISM: Artificial Sequence
<220> FEATURE:
<223> OTHER INFORMATION: Primer

<400> SEQUENCE: 194
gaggtgmwgc tkvwg                                                  15

<210> SEQ ID NO 195
<211> LENGTH: 24
<212> TYPE: DNA
<213> ORGANISM: Artificial Sequence
<220> FEATURE:
<223> OTHER INFORMATION: Primer

<400> SEQUENCE: 195
gaggtgmwgc tkvwgsagtc tgga                                        24

<210> SEQ ID NO 196
<211> LENGTH: 44
<212> TYPE: DNA
<213> ORGANISM: Artificial Sequence
<220> FEATURE:
<223> OTHER INFORMATION: Primer

<400> SEQUENCE: 196
cgagctcgga tccggcccag ccggccsagg tgmwgctkvw gsag                  44

<210> SEQ ID NO 197
<211> LENGTH: 15
<212> TYPE: DNA
<213> ORGANISM: Artificial Sequence
<220> FEATURE:
<223> OTHER INFORMATION: Primer
```

<400> SEQUENCE: 197
gacdgtgash rdrgt                                                              15

<210> SEQ ID NO 198
<211> LENGTH: 27
<212> TYPE: DNA
<213> ORGANISM: Artificial Sequence
<220> FEATURE:
<223> OTHER INFORMATION: Primer

<400> SEQUENCE: 198
gacdgtgash rdrgtbcctk srcccca                                                 27

<210> SEQ ID NO 199
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 88-33
<223> OTHER INFORMATION: n = a, c, t or g

<400> SEQUENCE: 199
gacdgtgash rdrgtbcctk srccccannn nnn                                          33

<210> SEQ ID NO 200
<211> LENGTH: 49
<212> TYPE: DNA
<213> ORGANISM: Artificial Sequence
<220> FEATURE:
<223> OTHER INFORMATION: Primer

<400> SEQUENCE: 200
agaaccgctg cctgaaccgc ctccaccact gacdgtgash rdrgtbcct                         49

<210> SEQ ID NO 201
<211> LENGTH: 14
<212> TYPE: DNA
<213> ORGANISM: Artificial Sequence
<220> FEATURE:
<223> OTHER INFORMATION: Primer

<400> SEQUENCE: 201
gahrtygtkm tsac                                                               14

<210> SEQ ID NO 202
<211> LENGTH: 24
<212> TYPE: DNA
<213> ORGANISM: Artificial Sequence
<220> FEATURE:
<223> OTHER INFORMATION: Primer

<400> SEQUENCE: 202
gahrtygtkm tsacmcarwc tmca                                                    24

<210> SEQ ID NO 203
<211> LENGTH: 50
<212> TYPE: DNA
<213> ORGANISM: Artificial Sequence
<220> FEATURE:
<223> OTHER INFORMATION: Primer

<400> SEQUENCE: 203
tcaggcagcg gttctagcgg cggtggcgga gahrtygtkm tsacmcarwc                        50

```
<210> SEQ ID NO 204
<211> LENGTH: 15
<212> TYPE: DNA
<213> ORGANISM: Artificial Sequence
<220> FEATURE:
<223> OTHER INFORMATION: Primer

<400> SEQUENCE: 204
katytccary ytkgt                                                15

<210> SEQ ID NO 205
<211> LENGTH: 27
<212> TYPE: DNA
<213> ORGANISM: Artificial Sequence
<220> FEATURE:
<223> OTHER INFORMATION: Primer

<400> SEQUENCE: 205
katytccary ytkgtscchb cdccgaa                                   27

<210> SEQ ID NO 206
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 22-27
<223> OTHER INFORMATION: n = a, c, t or g

<400> SEQUENCE: 206
yytkgtscch bcdccgaayg tnnnnnn                                   27

<210> SEQ ID NO 207
<211> LENGTH: 44
<212> TYPE: DNA
<213> ORGANISM: Artificial Sequence
<220> FEATURE:
<223> OTHER INFORMATION: Primer

<400> SEQUENCE: 207
cggggtaccg cggccgckat ytccaryytk gtscchbcdc cgaa                44

<210> SEQ ID NO 208
<211> LENGTH: 13
<212> TYPE: DNA
<213> ORGANISM: Artificial Sequence
<220> FEATURE:
<223> OTHER INFORMATION: Primer

<400> SEQUENCE: 208
caggctgttg tga                                                  13

<210> SEQ ID NO 209
<211> LENGTH: 24
<212> TYPE: DNA
<213> ORGANISM: Artificial Sequence
<220> FEATURE:
<223> OTHER INFORMATION: Primer

<400> SEQUENCE: 209
caggctgttg tgactcagga atct                                      24

<210> SEQ ID NO 210
```

```
<211> LENGTH: 46
<212> TYPE: DNA
<213> ORGANISM: Artificial Sequence
<220> FEATURE:
<223> OTHER INFORMATION: Primer

<400> SEQUENCE: 210
tcaggcagcg gttctagcgg cggtggcgga caggctgttg tgactc         46

<210> SEQ ID NO 211
<211> LENGTH: 14
<212> TYPE: DNA
<213> ORGANISM: Artificial Sequence
<220> FEATURE:
<223> OTHER INFORMATION: Primer

<400> SEQUENCE: 211
acctaggaca gtca                                            14

<210> SEQ ID NO 212
<211> LENGTH: 24
<212> TYPE: DNA
<213> ORGANISM: Artificial Sequence
<220> FEATURE:
<223> OTHER INFORMATION: Primer

<400> SEQUENCE: 212
acctaggaca gtcavyytgg ttcc                                 24

<210> SEQ ID NO 213
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 28-33
<223> OTHER INFORMATION: n = a, c, t or g

<400> SEQUENCE: 213
agtcavyytg gttccwctnc mgaamaynnn nnn                       33

<210> SEQ ID NO 214
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 35
<223> OTHER INFORMATION: n = a, c, t or g

<400> SEQUENCE: 214
cgggtaccgc ggccgcagtc avyytggttc cwcyncmgaa                40
```